(12) United States Patent
Hamada et al.

(10) Patent No.: US 11,192,121 B2
(45) Date of Patent: Dec. 7, 2021

(54) BLOOD COMPONENT SEPARATOR WITH SLIDER FOR SEALING

(71) Applicant: TRANSELL Co., Ltd., Tokyo (JP)

(72) Inventors: Nariyuki Hamada, Hiroshima (JP); Shuji Nakamura, Kanagawa (JP); Katsuyuki Sado, Gunma (JP); Kenta Kaneda, Gunma (JP)

(73) Assignee: TRANSELL Co., Ltd., Tokyo (JP)

( * ) Notice: Subject to any disclaimer, the term of this patent is extended or adjusted under 35 U.S.C. 154(b) by 694 days.

(21) Appl. No.: 16/071,357

(22) PCT Filed: Dec. 20, 2016

(86) PCT No.: PCT/JP2016/087953
§ 371 (c)(1),
(2) Date: Jul. 19, 2018

(87) PCT Pub. No.: WO2017/126279
PCT Pub. Date: Jul. 27, 2017

(65) Prior Publication Data
US 2019/0030545 A1 Jan. 31, 2019

(30) Foreign Application Priority Data
Jan. 21, 2016 (JP) .............................. JP2016-009739

(51) Int. Cl.
*B04B 5/04* (2006.01)
*A61M 1/02* (2006.01)
(Continued)

(52) U.S. Cl.
CPC ........... *B04B 5/0407* (2013.01); *A61M 1/029* (2013.01); *A61M 1/0272* (2013.01);
(Continued)

(58) Field of Classification Search
CPC . B04B 5/0407; B04B 11/04; B04B 2011/046; A61M 1/0272; A61M 1/3693;
(Continued)

(56) References Cited

U.S. PATENT DOCUMENTS

| 4,326,959 A | 4/1982 | Ferrara |
|---|---|---|
| 10,058,799 B2 | 8/2018 | Lee |

(Continued)

FOREIGN PATENT DOCUMENTS

| CN | 102438672 | 5/2012 |
|---|---|---|
| EP | 2495302 | 9/2012 |

(Continued)

OTHER PUBLICATIONS

WO 2014168311 Description Espacenet Machine Translation.*
(Continued)

*Primary Examiner* — Walter D. Griffin
*Assistant Examiner* — Shuyi S. Liu
(74) *Attorney, Agent, or Firm* — Hamre, Schumann, Mueller & Larson, P.C.

(57) ABSTRACT

A blood component separator (1) includes a blood storage vessel (20) that includes a first storage part (21) and a second storage part (22), a slider (30) movable from the first storage part to the second storage part, and a flow path (40*f*) for communicating an inside and an outside of the storage vessel. When the slider is in the first storage part, the first storage part and the second storage part are in communication with each other. When the slider is inserted into the second storage part, a liquid-tight seal is formed between the slider and the inner peripheral surface of the second storage part and the communication between the first storage part and the second storage part is blocked by the slider. The slider is movable in the second storage part while maintaining the liquid-tight seal between the slider and the inner (Continued)

peripheral surface of the second storage part. As the slider enters the second storage part, the blood component in the second storage part is pushed out of the storage vessel through the flow path.

16 Claims, 23 Drawing Sheets

(51) Int. Cl.
  *A61M 1/36* (2006.01)
  *B04B 11/04* (2006.01)
(52) U.S. Cl.
  CPC ............ *A61M 1/3693* (2013.01); *B04B 11/04* (2013.01); *A61M 2202/0439* (2013.01); *A61M 2202/10* (2013.01); *B04B 2011/046* (2013.01)
(58) Field of Classification Search
  CPC .......... A61M 1/029; A61M 2202/0439; A61M 2202/10; A61M 1/0281
  USPC ............................................. 494/76; 604/410
  See application file for complete search history.

(56) References Cited

U.S. PATENT DOCUMENTS

| | | | |
|---|---|---|---|
| 2009/0289014 A1* | 11/2009 | Hoeppner | ............ A61M 1/3696 210/741 |
| 2010/0256595 A1 | 10/2010 | Leach et al. | |
| 2011/0238029 A1 | 9/2011 | Biset et al. | |
| 2014/0205514 A1 | 7/2014 | Hwang | |
| 2016/0051747 A1* | 2/2016 | Wegener | ................. A61M 1/02 435/325 |
| 2016/0235906 A1 | 8/2016 | Takuwa et al. | |
| 2017/0189833 A1 | 7/2017 | Lee | |

FOREIGN PATENT DOCUMENTS

| | | | |
|---|---|---|---|
| EP | 2495302 A2 * | 9/2012 | ............ A61M 1/029 |
| EP | 2 842 619 | 4/2015 | |
| JP | 2015-054181 | 3/2015 | |
| KR | 101170146 | 7/2012 | |
| KR | 10-2015-0134894 | 12/2015 | |
| WO | 2010/061863 | 6/2010 | |
| WO | 2013/042862 | 3/2013 | |
| WO | 2014168311 | 10/2014 | |
| WO | WO-2014168311 A1 * | 10/2014 | ............ C12M 47/04 |
| WO | 2015/025912 | 2/2015 | |
| WO | 2015037845 | 3/2015 | |
| WO | 2015/045688 | 4/2015 | |

OTHER PUBLICATIONS

Office Action issued for Australian Patent Application No. 2016387808, dated Feb. 28, 2019, 8 pages.
Decision to Grant a Patent issued in corresponding Korean Patent Application No. 10-2018-7022344, dated Jun. 15, 2020, 2 pages with translation.
Office Action issued in corresponding Chinese Patent Application No. 201680079636.7, dated Apr. 21, 2020, 10 pages with translation.
Extended European Search Report for the corresponding European Patent Application No. 16886518.6, dated Aug. 16, 2019, 8 pages.

* cited by examiner

BLOOD COMPONENT SEPARATOR WITH SLIDER FOR SEALING

TECHNICAL FIELD

The present invention relates to a blood component separator for use in centrifugal separation of blood into blood components.

BACKGROUND ART

In these years, a blood component transfusion of transfusing only necessary components in blood instead of whole blood transfusion, blood plasma collection for producing blood plasma products, and the like are being carried out. For this purpose, blood component separation of centrifugally separating blood into components such as erythrocyte, leukocyte, platelet, and the like utilizing the difference in specific gravity and extracting necessary components is performed in blood programs.

Patent Literature 1 describes a device for use in centrifugal separation of blood. The device includes a blood storage vessel for storing blood. The storage vessel includes a first storage part, a second storage part, and a third storage part provided between the first storage part and the second storage part. The third storage part communicates with the first storage part and the second storage part. A first blocking member movable in the first storage part is provided in the first storage part, and a second blocking member movable in the second storage part is provided in the second storage part.

When blood is injected into the storage vessel and centrifugal separation is performed, blood is separated into an erythrocyte component to be stored in the first storage part, a blood plasma component to be stored in the second storage part, and a leukocyte component to be stored in the third storage part. Thereafter, the first blocking member is moved to close an opening on the first storage part side of the third storage part, and the second blocking member is moved to close an opening on the second storage part side of the third storage part. In this state, the leukocyte component in the third storage part is recovered through a hollow rod that holds the first blocking member.

With the device of Patent Literature 1, blood is centrifugally separated into three components such as an erythrocyte component, a blood plasma component, and a leukocyte component to be stored in three storage parts, respectively, and then communication between adjacent storage parts is blocked with the first and second blocking members. Therefore, a leukocyte component can be recovered without being mixed with other components.

CITATION LIST

Patent Literature

Patent Literature 1: WO 2015/025912

SUMMARY OF INVENTION

Technical Problem

In the device of Patent Literature 1, a syringe is connected to a rod that holds the first blocking member in the state where openings at both ends of the third storage part are closed with the first blocking member and the second blocking member, and the leukocyte component in the third storage part is sucked into the syringe. This method has a problem in that cells contained in the leukocyte component remain attached to the inner peripheral surface of the third storage part and the leukocyte component cannot be sufficiently recovered.

Patent Literature 1 describes a method of recovering the leukocyte component remaining in the third storage part by washing with physiological saline. Specifically, after sucking the leukocyte component from the third storage part into a syringe, instead of this syringe, a syringe that stores physiological saline is connected to the rod. Then, the physiological saline in the syringe is injected into the third storage part, the third storage part is washed with physiological saline, and then the physiological saline is sucked into the syringe.

This method, however, requires steps of injecting physiological saline into the third storage part and then sucking the physiological saline. Furthermore, for recovering the leukocyte component from the physiological saline that has been sucked into the syringe, the method further requires a step such as centrifugal separation or the like. Thus, there is a problem in that it takes a lot of time and effort for improving the recovery rate of the leukocyte component.

The present invention is intended to solve the above-described problems and to provide a blood component separator that allows a leukocyte component to be recovered efficiently.

Solution to Problem

A blood component separator of the present invention is for use in centrifugal separation of blood. The device includes a blood storage vessel that includes a first storage part and a second storage part; a slider movable from the first storage part to the second storage part; and a flow path for communicating an inside and an outside of the storage vessel. When the slider is in the first storage part, the first storage part and the second storage part are in communication with each other. When the slider is inserted into the second storage part, a liquid-tight seal is formed between the slider and an inner peripheral surface of the second storage part and the communication between the first storage part and the second storage part is blocked by the slider. The slider is movable in the second storage part while maintaining the liquid-tight seal between the slider and the inner peripheral surface of the second storage part. The device is configured so that, as the slider enters into the second storage part, a blood component in the second storage part is pushed out of the storage vessel through the flow path.

Advantageous Effects of Invention

According to the present invention, blood can be centrifugally separated in the state where the slider is in the first storage part. Then, when the slider is inserted into the second storage part, a leukocyte component of the second storage part can be pushed out of the storage vessel through the flow path. The slider scrapes the leukocyte component attached to the inner peripheral surface of the second storage part while moving in the second storage part. This improves the recovery rate of the leukocyte component.

For improving the recovery rate of the leukocyte component, steps of washing with physiological saline and centrifugally separating the physiological saline used in washing are required in the case of using a conventional device. These steps, however, are not necessary in the case of using the device of the present invention. Therefore, the present invention allows a leukocyte component to be recovered efficiently.

DESCRIPTION OF EMBODIMENTS

Figure 1:
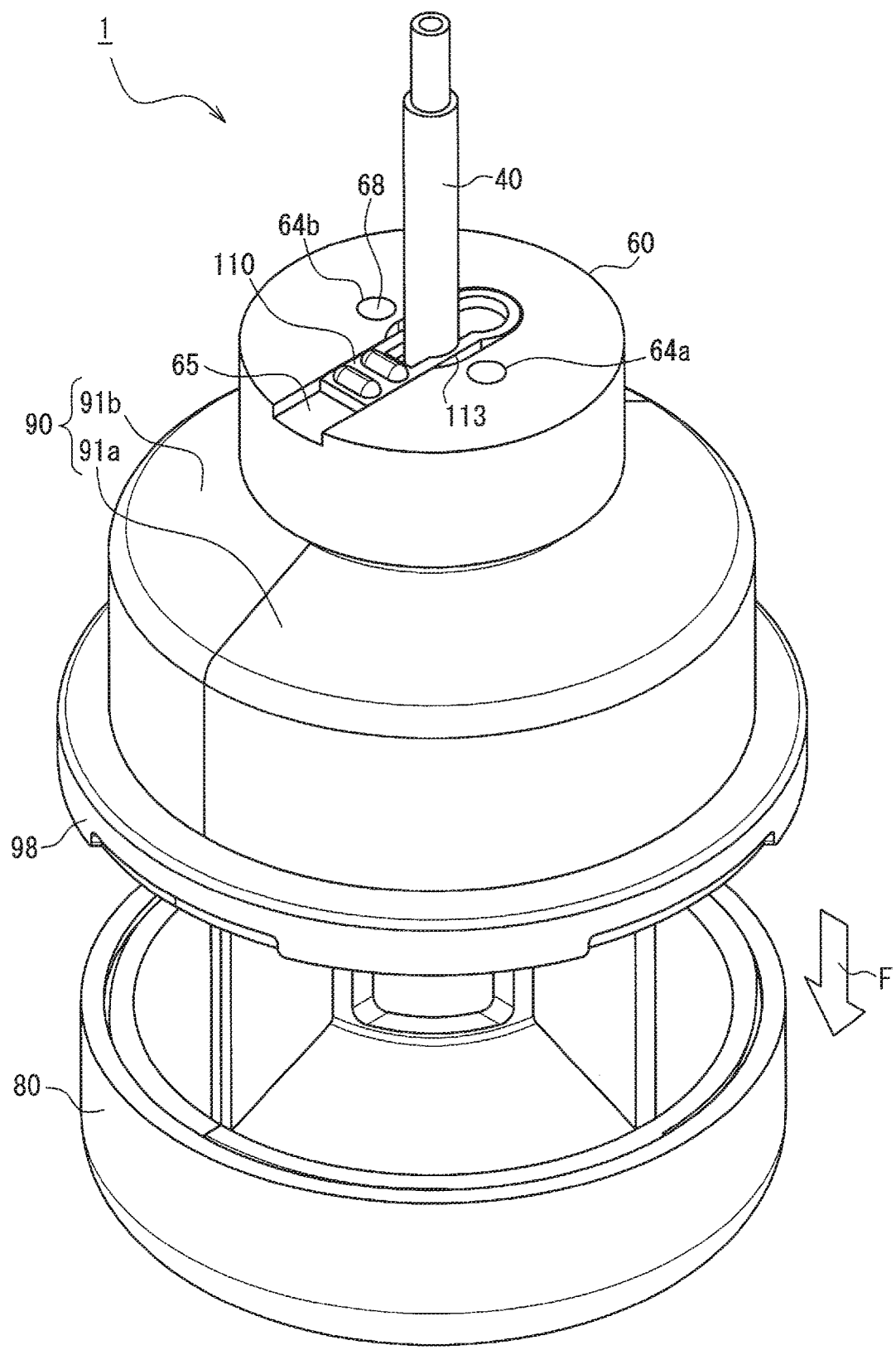
FIG. 1 is a perspective view of a blood component separator according to the first embodiment of the present invention.

The device according to one embodiment of the present invention may further include a first rod holding the slider and led out of the storage vessel. In this case, the flow path may be provided in the first rod. Holding the slider by the first rod is advantageous for facilitating the movement of the slider in the storage vessel. Providing the flow path in the first rod is advantageous for simplifying the structure of the device because a separate member for forming the flow path is unnecessary. Providing the flow path on the slider side is advantageous for recovering a leukocyte component of high purity and improving the recovery rate of the leukocyte component.

The device according to one embodiment of the present invention may further include a first locking mechanism that restricts movement of the slider in the first storage part toward the second storage part. This is advantageous in preventing a situation in which the slider moves unintentionally to block the communication between the first storage part and the second storage part.

The second storage part may include a cylinder part disposed adjacent to the first storage part. In this case, the liquid-tight seal part is preferably formed between the inner peripheral surface of the cylinder part and the slider.

The inner peripheral surface of the cylinder part is preferably a cylindrical surface. This is advantageous for forming a liquid-tight seal between the slider and the inner peripheral surface of the cylinder part with a simple structure.

The second storage part may include an auxiliary storage part communicating with the first storage part through the cylinder part. In this case, the auxiliary storage part may have a larger inner diameter than the cylinder part. Because the auxiliary storage part in which an erythrocyte component is stored after centrifugal separation has a relatively large inner diameter, the height of the storage vessel and the device can be reduced.

The second storage part may include an auxiliary storage part communicating with the first storage part through the cylinder part. In this case, a blocking member that can block the communication between the cylinder part and the auxiliary storage part may be provided in the second storage part. This makes it possible to insert the slider into the cylinder part and to push the leukocyte component in the cylinder part out of the storage vessel in the state where communication between the cylinder part and the auxiliary storage part is blocked with a blocking member. Blocking the communication between the cylinder part and the auxiliary storage part with the blocking member prevents the leukocyte component in the cylinder part and the erythrocyte component in the auxiliary storage part from being mixed.

Thus, according to the above-described preferred structure, the recovery rate of the leukocyte component can stably be improved.

The blocking member may be movable in the auxiliary storage part. In this case, when the blocking member is in the auxiliary storage part, the cylinder part and the auxiliary storage part are preferably in communication with each other. When the auxiliary storage part is fitted into an opening on the auxiliary storage part side of the cylinder part, the communication between the cylinder part and the auxiliary storage part is preferably blocked by the blocking member. Such a structure is advantageous for certainly switching the communication and blocking between the cylinder part and the auxiliary storage part with a relatively simple structure.

The device according to one embodiment of the present invention may include a second rod holding the blocking member and led out of the storage vessel. In this case, the flow path may be provided in the second rod. Holding the blocking member by the second rod is advantageous for facilitating the movement of the blocking member in the auxiliary storage part. Providing the flow path in the second rod is advantageous for simplifying the structure of the device because a separate member for forming the flow path is unnecessary.

The device according to one embodiment of the present invention may include a second locking mechanism for maintaining a state where the blocking member blocks the communication between the cylinder part and the auxiliary storage part. This is advantageous in preventing a situation in which the cylinder part communicates with the auxiliary storage part unintentionally.

The device according to one embodiment of the present invention may further include a vent port for communicating the first storage part and the outside of the storage vessel. According to such a preferred structure, as the slider enters into the second storage part, the outside air flows into the first storage part through the vent port. This is advantageous for facilitating the operation of pushing the blood component out of the storage vessel by moving the slider in the second storage part.

The second storage part may be provided with a volume adjusting mechanism that can adjust the volume of the storage vessel. According to such a preferred structure, regardless of the amount or the hematocrit value of the blood to be centrifugally separated, the position of a leukocyte component layer after centrifugal separation can coincide with a desired region (for example, cylinder part) in the second storage part. This is advantageous for improving the recovery rate of the leukocyte component.

The device according to one embodiment of the present invention may include a blood component recovery device configured to recover the blood component pushed out of the storage vessel through the flow path. In this case, the recovery device may include a first container, a second container, and a switching mechanism configured to selectively communicate the flow path with either the first container or the second container. According to such a preferred structure, the flow path can appropriately communicate with either the first container or the second container depending on the blood component pushed out from the second storage part through the flow path. This is advantageous for recovering a leukocyte component of high purity in which a blood plasma component and an erythrocyte component are substantially not mixed.

The present invention is described below in detail with reference to preferred embodiments. However, needless to say, the present invention is not limited to the following embodiments. For convenience of explanation, each of the drawings referred to in the following description is a simplified representation of the main components of the embodiments of the present invention. Furthermore, within the scope of the present invention, each member shown in the drawings described below can be changed or omitted.

1. First Embodiment 1.1. Structure of Blood Component Separator

The structure of a blood component separator (hereinafter, simply referred to as a "device") 1 according to the first embodiment of the present invention is described below.

Figure 2:
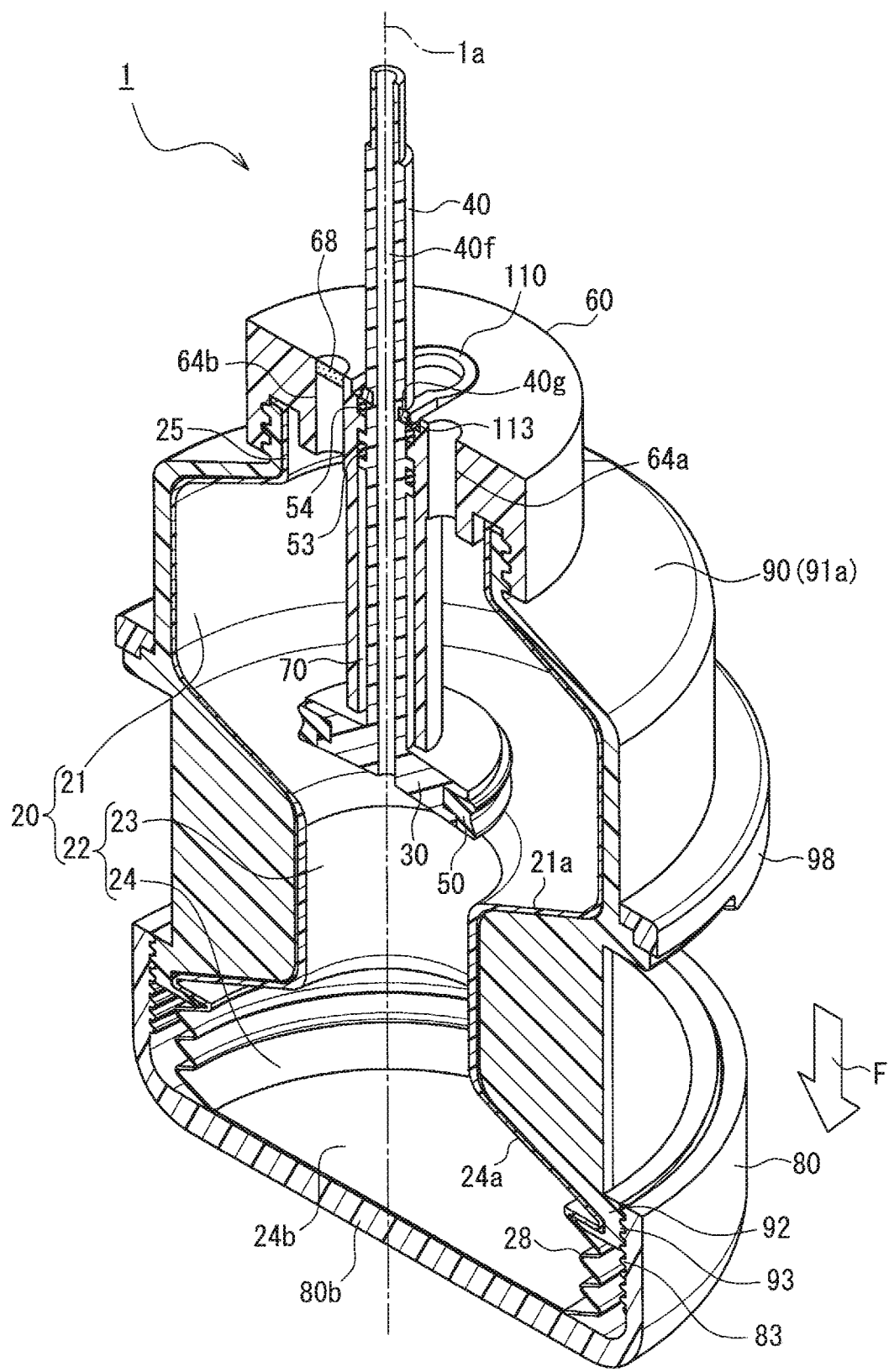
FIG. 2 is a cross sectional perspective view of the device according to the first embodiment of the present invention.

FIG. 1 is a perspective view of the device 1. FIG. 2 is a cross sectional perspective view taken along the vertical direction surface of the device 1. In FIG. 2, a dashed-dotted line 1a is the central axis of the device 1. For the convenience of the following description, the direction parallel to the central axis 1a is referred to as the "vertical direction" and the direction parallel to the plane orthogonal to the central axis 1a is referred to as the "horizontal direction". The direction along the straight line orthogonal to the center axis 1a is referred to as the "radial direction", and the direction rotating around the central axis 1a is referred to as the "circumferential direction".

As shown in FIG. 2, the device 1 includes a blood storage vessel (hereinafter, simply referred to as a "storage vessel") 20 for storing blood. The device 1 is for use in centrifugal separation of blood stored in the storage vessel 20 into blood components.

The storage vessel 20 includes a first storage part 21 and a second storage part 22. The second storage part 22 includes a cylinder part 23 and an auxiliary storage part 24. From the top to the bottom, the first storage part 21, the cylinder part 23, and the auxiliary storage part 24 are disposed in this order, and these components are in communication with each other. That is, the cylinder part 23 is in communication with the first storage part 21 and the auxiliary storage part 24, and the first storage part 21 and the auxiliary storage part 24 are in communication with each other through the cylinder part 23. In general, the device 1 is used in the state where the auxiliary storage part 24 is located at the lowermost position with the central axis 1a being the vertical direction. An opening 25 having a substantially cylindrical shape projects upward from the center of the upper surface of the first storage part 21. The opening 25, the first storage part 21, the cylinder part 23, and the auxiliary storage part 24 are disposed coaxially with the central axis 1a.

Blood is injected into the storage vessel 20 through the opening 25. The device 1 storing blood in the storage vessel 20 is to be mounted to a centrifuge so that a centrifugal force acts in the direction of arrow F in FIGS. 1 and 2. During centrifugal separation, each blood component can freely move from the first storage part 21 through the cylinder part 23 to the auxiliary storage part 24 or vice versa. After the centrifugal separation, an erythrocyte component having a relatively high specific gravity is stored in the auxiliary storage part 24, a blood plasma component having a relatively low specific gravity is stored in the first storage part 21, and a buffy coat (a leukocyte component layer) containing a leukocyte component and platelet is stored in the cylinder part 23. The volumes of the first storage part 21, cylinder part 23, and auxiliary storage part 24 are set such that each of the blood components is stored in a predetermined part of the storage vessel 20 after the centrifugal separation.

The first storage part 21 has a hollow substantially cylindrical shape.

The auxiliary storage part 24 has a hollow substantially cylindrical shape as a whole. The outer diameter and the inner diameter of the auxiliary storage part 24 are substantially the same as the outer diameter and the inner diameter of the first storage part 21. It is to be noted that a bellows structure 28 that can be expanded and/or compressed in the vertical direction is provided on the cylindrical side wall of the auxiliary storage part 24. The bellows structure 28 is formed by periodically bending the side wall of the auxiliary storage part 24 in a zigzag manner. Expanding and compressing the bellows structure 28 in the vertical direction makes it possible to increase or reduce the volume of the auxiliary storage part 24 and further the volume of the storage vessel 20. That is, the bellows structure 28 functions as a "volume adjusting mechanism" that can adjust the volume of the storage vessel 20.

The cylinder part 23 also has a hollow substantially cylindrical shape. The inner peripheral surface of the cylinder part 23 is a cylindrical surface having a constant inner diameter in the direction of the central axis 1a. This is advantageous for forming a liquid-tight seal between the slider 30 and the inner peripheral surface of the cylinder part 23 when the slider 30 moves downward in the cylinder part 23 as described below. Furthermore, because such a structure allows each blood component to be moved upward or downward through the cylinder part 23 easily during the centrifugal separation, the separability of each blood component is improved, which is advantageous for improving the recovery rate of a leukocyte component.

The inner diameter of the cylinder part 23 is smaller than the inner diameter of each of the first storage part 21 and the auxiliary storage part 24. Because the proportion of the leukocyte component in blood is relatively small, by reducing the inner diameter of the cylinder part 23, the thickness (vertical dimension) of a buffy coat after the centrifugal separation can be made relatively large. This is advantageous for recovering the leukocyte components efficiently.

The inner surface of a lower side wall (a wall on the cylinder part 23 side) 21a of the first storage part 21 is preferably formed into a funnel shape (i.e., a conical shape or a tapered shape) inclined so as to descend (so as to approach the cylinder part 23) as approaching the central axis 1a. This is advantageous for a blood component such as erythrocyte having a relatively high specific gravity in the first storage part 21 to pass through the cylinder part 23 and to move to the auxiliary storage part 24 during the centrifugal separation.

Similarly, the inner surface of an upper side wall (the wall on the cylinder part 23 side) 24a of the auxiliary storage part 24 is preferably formed into a funnel shape (i.e., a conical shape or a tapered shape) inclined so as to rise (so as to approach the cylinder part 23) as approaching the central axis 1a. This is advantageous for a blood component such as blood plasma having a relatively low specific gravity in the auxiliary storage part 24 to pass through the cylinder part 23 and to move to the first storage part 21 during the centrifugal separation.

The material of the storage vessel 20 preferably has a mechanical strength such that its shape does not change (i.e., it has shape retainability) when blood is stored. Furthermore, the material preferably has relatively high rigidity so that the deformation of the storage vessel 20 can be kept small even with a centrifugal force acting on the blood in the centrifugal separation. However, the bellows structure 28 preferably has enough flexibility to expand and compress. In addition, the material of the storage vessel 20 preferably has transparency so that the blood in the blood storage vessel 20 can be visually recognized from the outside. From such a viewpoint, although there is no limitation, resin materials such as low density polyethylene (LDPE), polypropylene (PP), and ethylene-vinylacetate copolymer resin (EVA) can be used, for example.

The method of producing a storage vessel 20 is not limited. In the present embodiment, the whole of the storage vessel 20 including the bellows structure 28 is integrally molded as a single piece by a blow molding method or the like using a resin material. As compared to the case where separately prepared parts are joined together, integrally molding the seamless storage vessel 20 is advantageous for reducing the possibility that the blood pressurized by the centrifugal force during the centrifugal separation leaks out of the storage vessel 20. It is also advantageous for simplification of the production of the storage vessel 20 and reduction in cost.

As a matter of course, the storage vessel 20 can be produced by integrally connecting separately prepared members in a liquid-tight manner. For forming a liquid-tight seal between the inner peripheral surface of the cylinder part 23 and the slider 30 (details are described below), it is desirable to improve the tolerance of the cylindrical surface that configures the inner peripheral surface of the cylinder part 23. From this point of view, it is preferable to form the inner peripheral surface of the cylinder part 23 with high accuracy using a die by injection molding or the like. For achieving this, the whole of the cylinder part 23 may be formed by the injection molding. Alternatively, a cylindrical member that configures the inner peripheral surface of the cylinder part 23 may be formed by the injection molding and the thus obtained cylindrical member may be fitted into the storage vessel 20 separately prepared by the blow molding method. In the injection molding, for improving molding accuracy, a relatively hard material such as polycarbonate, polyethylene, polyester, polymethylpentene, methacryl, an ABS resin (acrylonitrile butadiene styrene copolymer), a PET resin (polyethylene terephthalate), PVC (polyvinyl chloride) or the like is preferably used.

Figure 3:
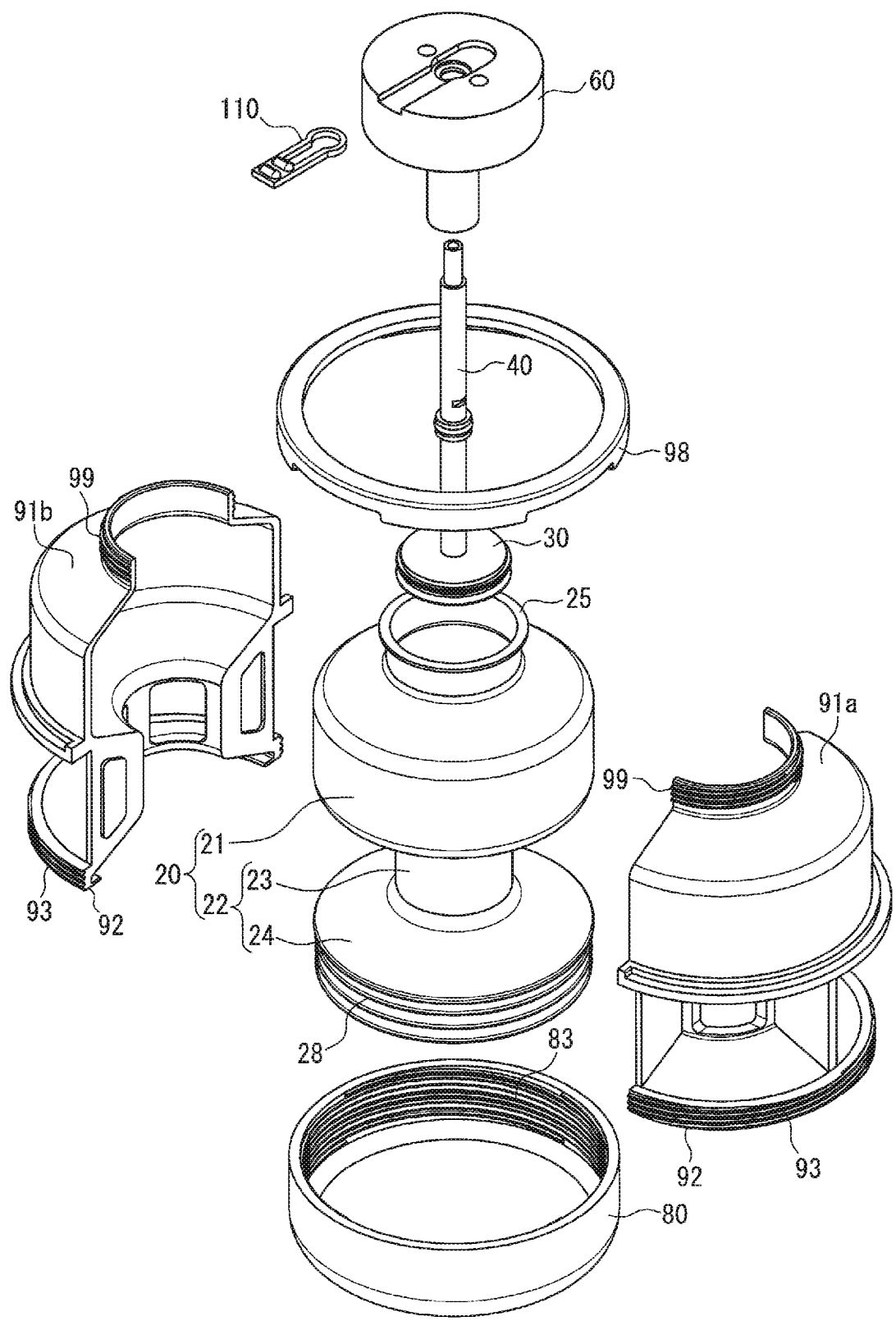
FIG. 3 is an exploded perspective view of the device according to the first embodiment of the present invention.

FIG. 3 is an exploded perspective view of the device 1. As can be understood from FIGS. 1 to 3, a support member 90 is attached to the outer peripheral surface of the storage vessel 20. The support member 90 has an inner peripheral surface substantially along the outer peripheral surface of the storage vessel 20 and covers the storage vessel 20 from the upper end thereof (a cylindrical part surrounding the opening 25) to the bellows structure 28. The support member 90 includes two support halfs 91a and 91b (see FIG. 3). The support halfs 91a and 91b are attached to the outer peripheral surface of the storage vessel 20 so as to sandwich the storage vessel 20 therebetween. Thereafter, a locking ring 98 is externally fitted into the support halfs 91a and 91b from above. Thus, the support half 91a and the support half 91b are integrated on the storage vessel 20. Thereafter, a bottom cap 80 is attached to the lower end of the support member 90 and a top cap 60 is attached to the support member 90.

The support member 90 (support halfs 91a, 91b) includes a skirt part 92 at its lower end. The skirt part 92 has a cylindrical shape and surrounds the bellows structure 28 of the storage vessel 20. A male screw 93 is formed on the outer peripheral surface of the skirt part 92.

The bottom cap 80 has a bottomed cylindrical shape. A female screw 83 is formed on the inner peripheral surface of the cylindrical part of the bottom cap 80. The female screw 83 is screwed with the male screw 93 of the support member 90.

As the bottom cap 80 is rotated with respect to the support member 90 and the male screw 93 is screwed into the female screw 83, the bellows structure 28 of the storage vessel 20 is compressed and deformed in the vertical direction between the support member 90 and the bottom cap 80. When the bellows structure 28 is compressed and deformed, the volume of the auxiliary storage part 24 is decreased and the volume of the storage vessel 20 is decreased. By adjusting the screwing depth of the male screw 93 with respect to the female screw 83, the compressive deformation amount of the bellows structure 28 can be adjusted, and eventually the volume of the storage vessel 20 can be adjusted. The male screw 93 of the support member 90 and the female screw 83 of the bottom cap 80 configure a "bellows adjusting mechanism" that adjusts the amount of expansion and compression of the bellows structure 28. A scale indicating the rotational position of the bottom cap 80 or the engagement depth of the male screw 93 and the female screw 83 may be provided on the bottom cap 80 or the support member 90.

The support member 90 and the bottom cap 80 prevent the storage vessel 20 (especially, the bellows structure 28 and the cylinder part 23) from being deformed by the centrifugal force acting on the blood in the blood storage vessel 20 during the centrifugal separation. Therefore, the support member 90 and the bottom cap 80 each preferably have a sufficient mechanical strength to be substantially regarded as a rigid body. In addition, the support member 90 and the bottom cap 80 preferably have transparency so that the blood in the storage vessel 20 can be seen through the support member 90 and the bottom cap 80. From such a viewpoint, examples of the material of the support member 90 and the bottom cap 80 include resin materials such as polycarbonate, polypropylene, rigid polyvinyl chloride, polyoxymethylene, and polyether ether ketone.

As shown in FIG. 2, the device 1 includes the slider 30 in the first storage part 21. The slider 30 is held at the lower end of a rod 40.

Figure 4A:
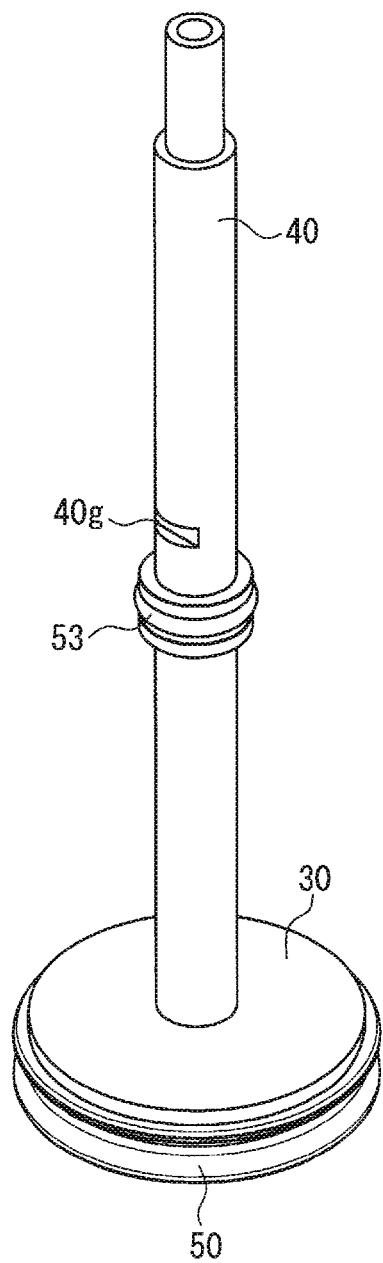
FIG. 4A is a perspective view showing a slider and a rod in the first embodiment of the present invention.
Figure 4B:
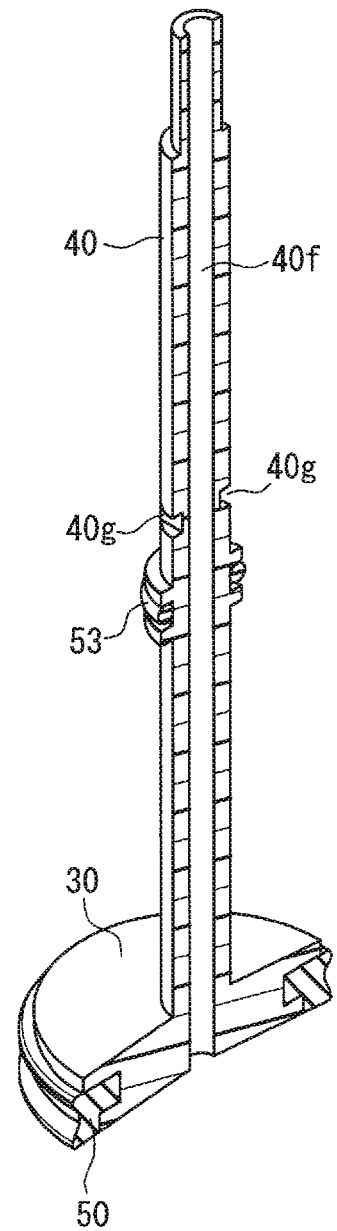
FIG. 4B is a cross sectional perspective view of FIG. 4A.

FIG. 4A is a perspective view of the slider 30 and the rod 40, and FIG. 4B is a cross sectional perspective view thereof. The slider 30 has a substantially disc shape (or a thin substantially cylindrical shape). An annular gasket 50 as a seal member is attached to the cylindrical outer peripheral surface of the slider 30. The slider 30 is provided with a through hole penetrating the slider 30 in the vertical direction at the center thereof.

The rod 40 is a bar-like member having a hollow cylindrical shape. The lower end of the rod 40 is connected to the center of the upper surface of the slider 30. As shown in FIG. 4B, the lumen of the rod 40 communicates with the through hole of the slider 30 to form a flow path 40f. The flow path 40f penetrates the slider 30 and the rod 40 in the vertical direction. On the outer peripheral surface of the rod 40, a pair of locking grooves 40g extending in the horizontal direction are formed. The locking groove 40g is not required to be divided in the circumferential direction, and may be, for example, an annular groove continuous in the circumferential direction. An O ring 53 is attached to the outer peripheral surface of the rod 40. The O ring 53 is positioned between the locking groove 40g and the slider 30.

In the present embodiment, the slider 30 (excluding the gasket 50) and the rod 40 are integrally produced as a single piece as a whole. The present invention, however, is not limited thereto, and the separately prepared slider 30 and the rod 40 may be combined.

Figure 5A:
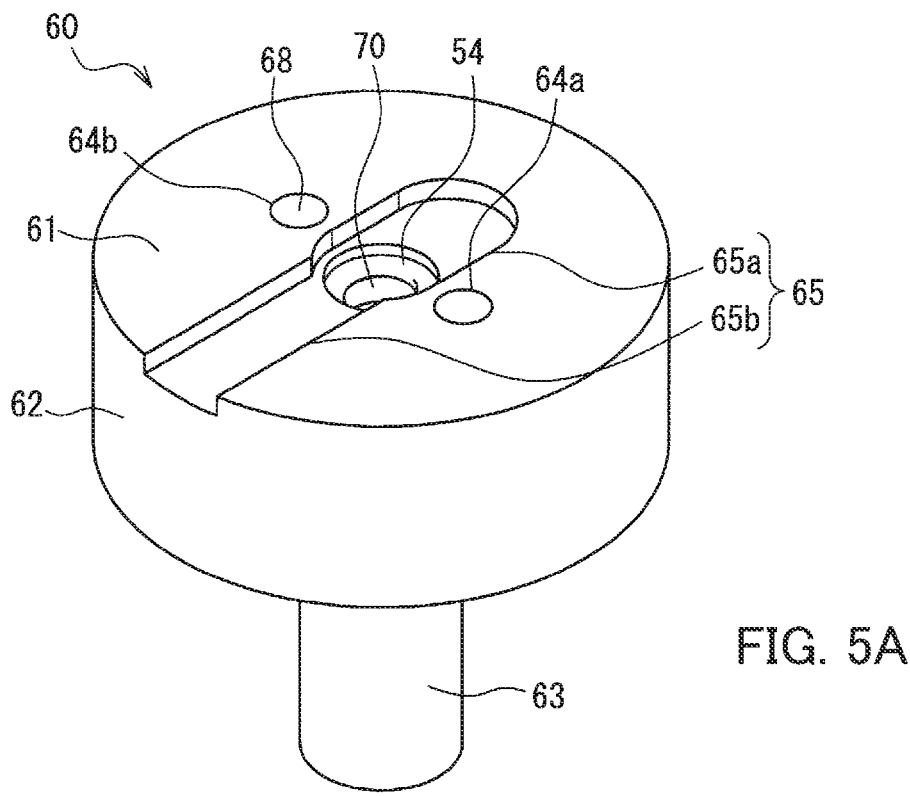
FIG. 5A is a perspective view showing a top cap in the first embodiment of the present invention.
Figure 5B:
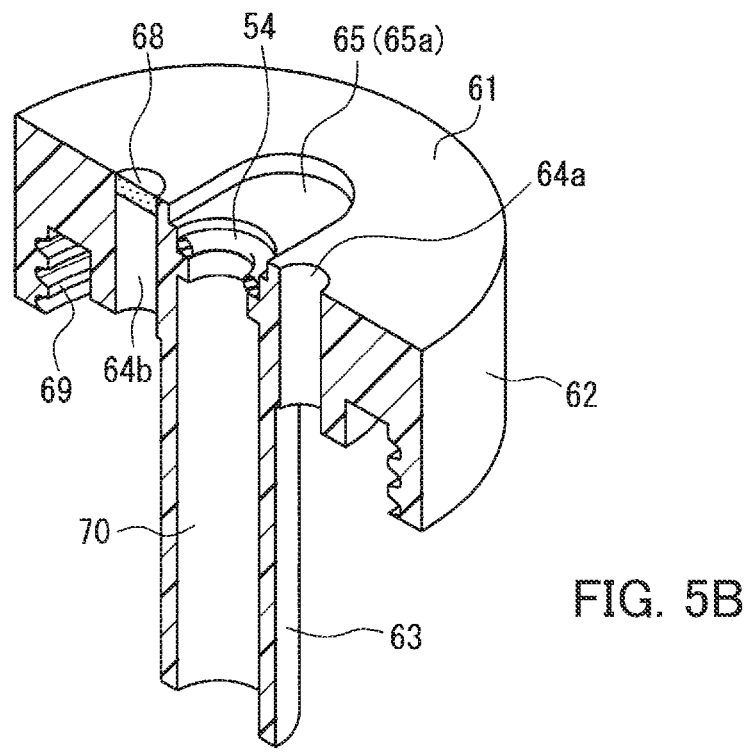
FIG. 5B is a cross sectional perspective view of FIG. 5A.

FIG. 5A is a perspective view of a top cap 60, and FIG. 5B is a cross sectional perspective view thereof. The top cap 60 includes a circular top plate 61, a cylindrical outer peripheral wall 62 extending downward from the outer peripheral edge of the top plate 61, and a guide tube 63 extending downward from the lower surface of the top plate 61.

A groove 65 extending straight is provided on the upper surface of the top plate 61. The width of the groove 65 is not constant, and the groove 65 includes a wide part 65a having a relatively wide width and a narrow part 65b having a relatively narrow width. The wide part 65a is provided at the center of the top plate 61 and the narrow part 65b connects the wide part 65a and the outer peripheral edge of the top plate 61.

A guide hole 70 penetrates the top plate 61 and the guide tube 63 in the vertical direction. The guide hole 70 is provided coaxially with the top plate 61 in the wide part 65a of the groove 65. The edge of the opening of the guide hole 70 facing upward is slightly expanded, which forms an annular dent. The O ring 54 is attached to the inside of the dent.

Two through holes 64a and 64b penetrating the top plate 61 in the vertical direction are provided on the top plate 61. The through holes 64a and 64b are provided in the top plate 61 in a region where the groove 65 is not formed.

The through hole 64a is used as an injection port for injecting blood into the storage vessel 20. After injecting blood into the storage vessel 20, the injection port 64a is sealed with a stopper (not shown) or the like.

The through hole 64b is used as a vent port. The vent filter 68 is provided in the through hole 64b. The vent filter 68 is a filter having a property of allowing gas to pass but not allowing liquid, bacteria, and the like to pass. The vent port 64b allows gas communication between the inside of the storage vessel 20 (particularly, first storage part 21) and the outside world through the vent filter 68.

On the inner peripheral surface of the outer peripheral wall 62, a female screw 69 is provided to be engaged with a male screw 99 (see FIG. 3) provided on the support member 90 (support halfs 91a and 91b).

Figure 6:
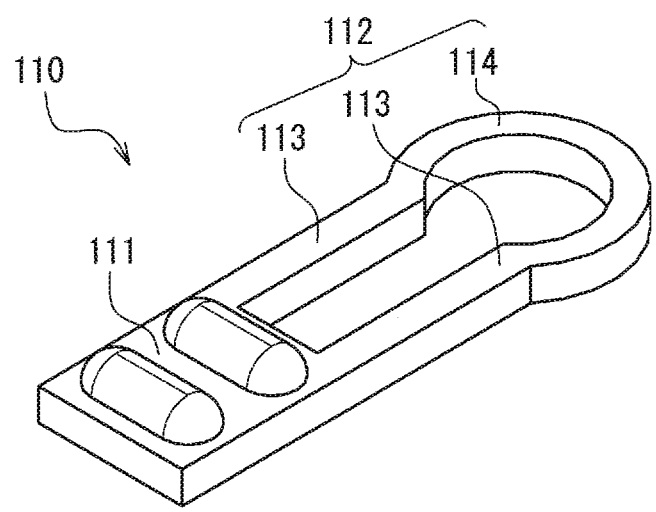
FIG. 6 is a perspective view showing a locking member in the first embodiment of the present invention.

FIG. 6 is a perspective view of a locking member 110. The locking member 110 includes a substantially rectangular thin plate-like operation part 111 and a substantially "U"-shaped frame 112 provided on one side of the operation part 111. The frame 112 includes a diameter-enlarged part 114 at the tip end and two parallel locking bars 113 parallel to each other between the diameter-enlarged part 114 and the operation part 111. While the diameter-enlarged part 114 has a substantially circular shape in the present embodiment, the shape of the diameter-enlarged part 114 is not limited thereto, and the diameter-enlarged part 114 may have any shape such as an elliptical shape, a regular hexagonal shape (see FIG. 19 described below), a regular octagonal shape, or the like. The inner diameter of the diameter-enlarged part 114 (the diameter of the inscribed circle of the diameter-enlarged part 114) is substantially equal to or slightly larger than the outer diameter of the rod 40 (see FIG. 4A). The outside dimension of the diameter-enlarged part 114 is larger than the outside dimension of the two locking bars 113. The distance between the two locking bars 113 is smaller than the inner diameter of the diameter-enlarged part 114 and smaller than the outer diameter of the rod 40. As described below, the two locking bars 113 are configured to be engageable with a locking groove 40g formed on the rod 40 (see FIGS. 4A and 4B).

As can be understood from FIGS. 2 and 3, the slider 30 held by the rod 40 and the top cap 60 are, in summary, attached to the storage vessel 20 as described below.

The support member 90 is attached to the storage vessel 20. The rod 40 is inserted into the guide hole 70 of the top cap 60 from below. The slider 30 is inserted into the opening 25 of the storage vessel 20, and the top cap 60 is screwed to the upper end of the support member 90. The opening 25 is covered with the top plate 61. The rod 40 penetrates the top cap 60 and projects upward. The rod 40 is inserted into the diameter-enlarged part 114 of the locking member 110. Then, the locking member 110 is fitted into the groove 65 formed on the upper surface of the top cap 60. More specifically, the diameter-enlarged part 114 and the operation part 111 of the locking member 110 are fitted into the wide part 65a and the narrow part 65b of the groove 65, respectively. The position of the rod 40 in the vertical direction is adjusted so that the locking groove 40g provided on the rod 40 is positioned at the same level as the locking member 110. Then, the locking member 110 is moved in the groove 65, and the locking bar 113 of the locking member 110 is fitted into the locking groove 40g of the rod 40.

Figure 7:
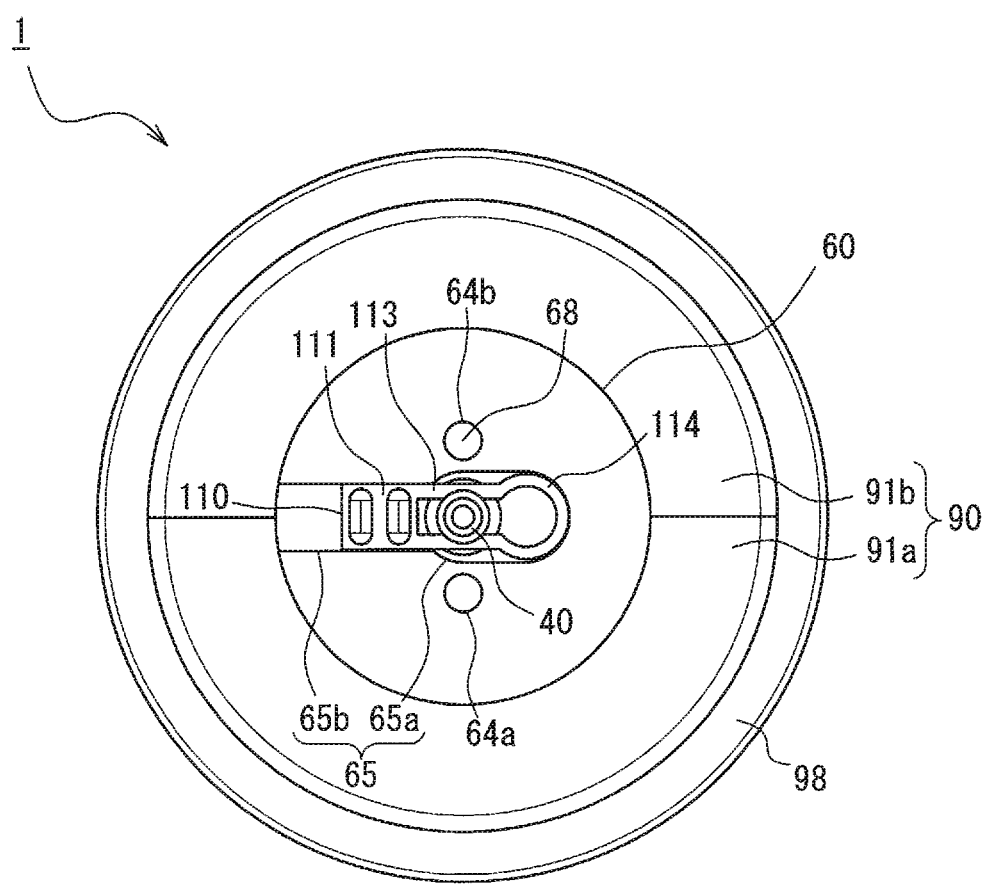
FIG. 7 is a plan view of the device according to the first embodiment of the present invention in the state where a locking mechanism for slider is in the locked state.

FIG. 7 is a plan view of the device 1 assembled in this manner. The rod 40 is positioned between the locking bars 113 of the locking member 110. FIGS. 1 and 2 each show the device 1 in the state where the locking member 110 is in the position of FIG. 7. As shown in FIG. 2, the locking bar 113 is engaged with the locking groove 40g of the rod 40. This prevents the rod 40 and the slider 30 held by the rod 40 from descending. In this manner, the locking member 110 and the locking groove 40g of the rod 40 to be engaged with the locking member 110 configure a "locking mechanism for slider 30". Switching between activation and invalidation of the lock by the locking mechanism can be achieved by moving the locking member 110 in the groove 65 in the horizontal direction. When the rod 40 is positioned between the locking bars 113 and the locking bar 113 is engaged with the locking groove 40g as shown in FIG. 7, the locking mechanism is in the locked state. When the rod 40 is positioned in the diameter-enlarged part 114, the locking mechanism is in the unlocked state. The movement of the locking member 110 can be performed by pressing a finger against the operation part 111.

When the locking mechanism is in the locked state, as shown in FIG. 2, the slider 30 held at the lower end of the rod 40 is in the air in the first storage part 21 without being in contact with the inner peripheral surface of the first storage part 21. The position of the slider 30 shown in FIG. 2 is referred to as the "initial position" of the slider 30.

Unless the engagement (locked state) between the locking member 110 (locking bar 113) and the rod 40 is released, even if a downward force is applied to the rod 40 or gravity or a centrifugal force acts on the rod 40 and the slider 30, the slider 30 does not descend from the initial position. The locking mechanism is advantageous for stably holding the slider 30 in the initial position. Thus, the communication between the first storage part 21 and the second storage part 22 (the cylinder part 23 and the auxiliary storage part 24) is ensured. This is advantageous for a reliable flow of blood from the first storage part 21 to the second storage part 22 when blood is injected from the opening 25 of the storage vessel 20. In addition, such a structure is advantageous for centrifugal separation of blood into a blood plasma component to be stored in the first storage part 21, a leukocyte component to be stored in the cylinder part 23, and an erythrocyte component to be stored in the auxiliary storage part 24.

The state where the slider 30 is in the initial position and the locking member 110 and the rod 40 are engaged (locked state) is referred to as the "initial state" (FIGS. 1, 2, and 7).

O rings 53 and 54 liquid-tightly seal the gap between the outer peripheral surface of the rod 40 and the inner peripheral surface of the guide hole 70 of the top cap 60. Furthermore, the top cap 60 liquid-tightly seals the opening 25 at the upper end of the storage vessel 20. Therefore, the space in the storage vessel 20 is liquid-tightly sealed except for the flow path 40f provided in the slider 30 and the rod 40 and the through holes 64a and 64b of the top cap 60.

The material of the slider 30 is preferably a hard material that can be considered as a substantially rigid body so that the gasket 50 can form a liquid-tight seal with the inner peripheral surface of the cylinder part 23 (the details are described below). Specifically, as the material of the slider 30, for example, a resin material such as polycarbonate (PC), polypropylene (PP), an ABS (acrylonitrile butadiene styrene copolymer) resin, polyethylene (PE), or an ethylene-vinyl acetate copolymer resin (EVA) can be used. Furthermore, for suppressing erythrocyte from attaching to the slider 30, an inclined surface such as a conical surface may be provided on the upper surface of the slider 30, or coating may be applied to the upper surface of the slider 30.

As the gasket 50, a gasket similar to a gasket that can be attached to the tip end of a plunger (pusher) of a common syringe can be used. As the O rings 53 and 54, a general-purpose O-ring that can form a liquid-tight seal can be used. The materials of the gasket 50 and the O rings 53 and 54 are not particularly limited, and a material having rubber elasticity (also referred to as elastomer) such as rubber including natural rubber, isoprene rubber, and silicone rubber or a thermoplastic elastomer including styrene elastomer, olefin elastomer, and polyurethane elastomer can be used.

In the present embodiment, the gasket 50 is attached to the slider 30 as a sealing material. The present invention, however, is not limited thereto, and any sealing material that can form a liquid-tight seal with the inner peripheral surface of the cylinder part 23 can be attached to the slider 30. For example, any 0 ring similar to the O rings 53 and 54 may be attached to the outer peripheral surface of the slider 30.

1.2. Usage

The usage of the device 1 is described.

First, blood (bone marrow aspirate) to be subjected to centrifugal separation is collected. The method of collecting the blood can be any method, and, for example, a certain amount (for example, about 100 ml to 400 ml) of the bone marrow aspirate may be collected by puncturing a syringe preliminarily moistened with heparin into the bone marrow at a dozen places.

Subsequently, the amount and the hematocrit value of the collected blood are measured. On the basis of the amount and the hematocrit value of the blood, the amount of the erythrocyte component and the amount of the blood plasma are calculated.

An empty device 1 (see FIGS. 1, 2, and 7) in the initial state is prepared. The bottom cap 80 is rotated to adjust the compressive deformation amount of the bellows structure 28. The compressive deformation amount is determined on the basis of the amounts of the erythrocyte component and the blood plasma calculated earlier such that a buffy coat after centrifugal separation is formed in the cylinder part 23 of the storage vessel 20. A cap (not shown) for closing the flow path 40f is attached to the upper end of the rod 40.

Subsequently, the collected blood is injected into the storage vessel 20 through the injection port 64*a*. As the blood is injected, the air in the storage vessel 20 flows out of the storage vessel 20 through the vent port 64*b*. Thus, even when the flow path 40*f* is closed, blood can be injected easily. Thereafter, the injection port 64*a* is sealed.

Subsequently, the device 1 filled with blood is subjected to a centrifuge to perform centrifugal separation. The centrifugal force acts in the direction of the arrow F shown in FIGS. 1 and 2 in parallel to the central axis 1*a*. The blood is centrifugally separated into the blood plasma component to be stored in the first storage part 21, the buffy coat (the leukocyte component and the platelet) to be stored in the cylinder part 23, and the erythrocyte component to be stored in the auxiliary storage part 24.

In the initial state, the locking member 110 is engaged with the rod 40 that holds the slider 30, and the locking mechanism is in the locked state where the locking mechanism is effectively functioned. Thus, even when the centrifugal force F acts during centrifugal separation, the slider 30 does not move downward from the initial position.

After the centrifugal separation, the device 1 is taken out from the centrifuge. The position of the buffy coat in the vertical direction may be finely adjusted by rotating the bottom cap 80 as necessary after the centrifugal separation so that the buffy coat is accurately arranged in the cylinder part 23.

Subsequently, the blood component recovery device 150 (see FIG. 11, details are described below) is connected to the upper end of the rod 40.

Figure 8:
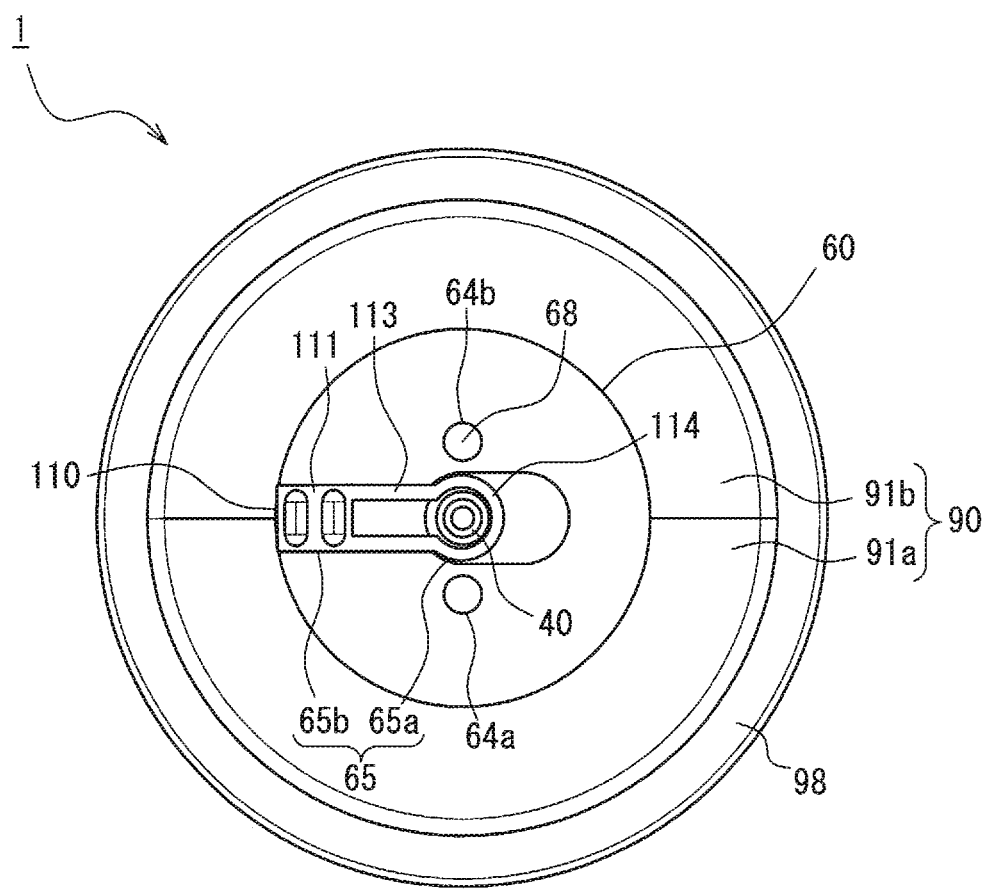
FIG. 8 is a plan view of the device according to the first embodiment of the present invention in the state where a locking mechanism for slider is in the unlocked state.

Subsequently, as shown in FIG. 8, the locking member 110 is moved in the groove 65 in the horizontal direction so that the rod 40 positions in the diameter-enlarged part 114. As a result, the engagement between the locking lever 113 of the locking member 110 and the locking groove 40*g* of the rod 40 is released (unlocked state).

Figure 9:
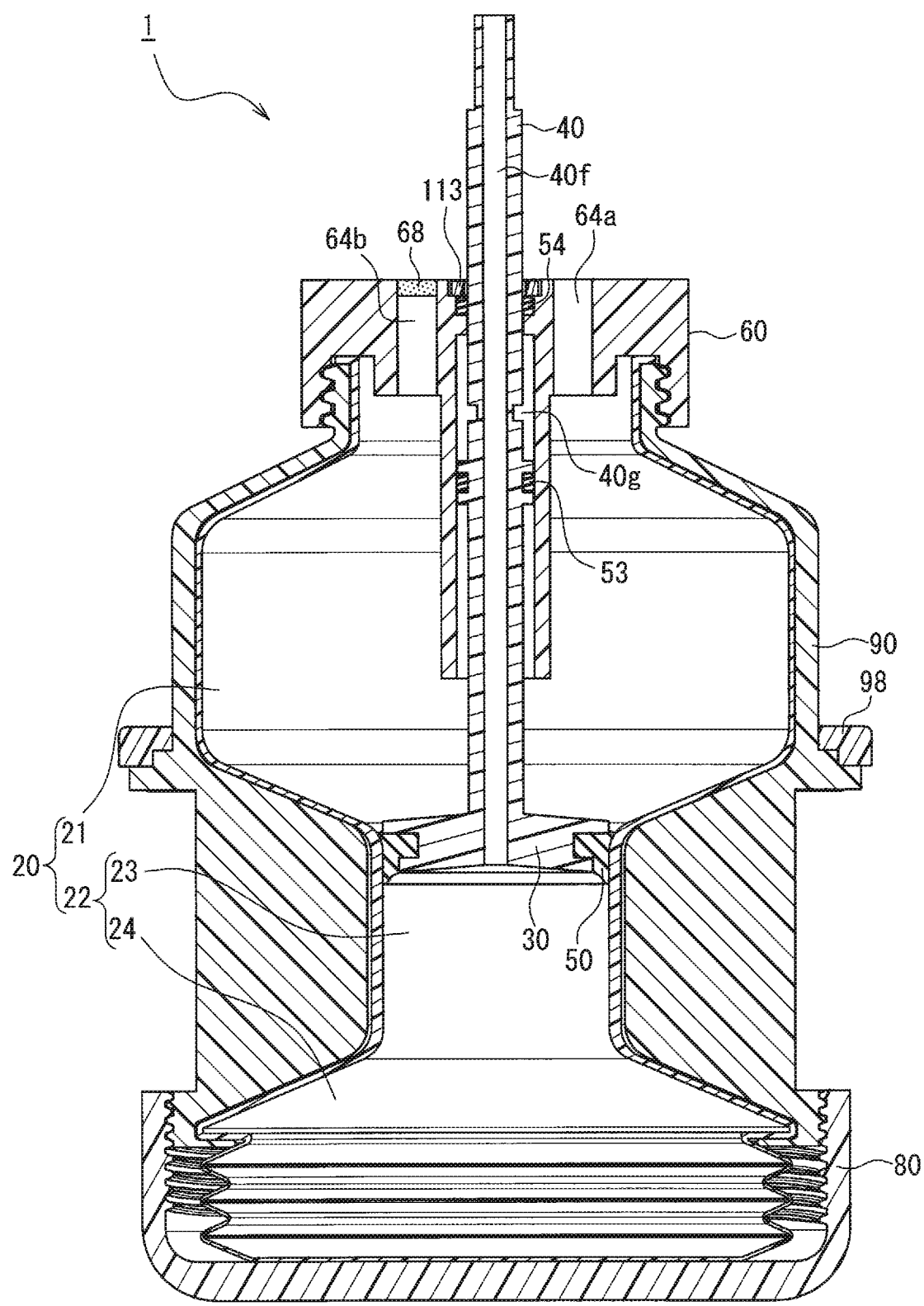
FIG. 9 is a cross sectional view of a device according to a first embodiment of the present invention in the state where a slider is fitted into an opening on the first storage part side of a cylinder part.

Subsequently, the rod 40 is pushed downward. Together with the rod 40, the slider 30 provided at the lower end of the rod 40 also moves downward. As shown in FIG. 9, the slider 30 is fitted into an upper opening (an opening on the first storage part 21 side) of the cylinder part 23. A liquid-tight seal is formed between the gasket 50 provided on the slider 30 and the inner peripheral surface of the cylinder part 23. As a result, the communication between the first storage part 21 and the second storage part 22 (the cylinder part 23 and the auxiliary storage part 24) is liquid-tightly blocked by the slider 30.

The rod 40 is further pushed downward. The slider 30 moves downward in the cylinder part 23 while maintaining the liquid-tight seal between the slider 30 and the inner peripheral surface of the cylinder part 23. As the slider 30 enters the cylinder part 23 (i.e., as the slider 30 moves away from the first storage part 21), the volume of the second storage part 22 decreases. Thus, the blood component (e.g., leukocyte component) in contact with the lower surface of the slider 30 flows out of the storage vessel 20 through the flow path 40*f*. In accordance with the descent of the slider 30, the outside air flows into the first storage part 21 through the vent port 64*b*, and a negative pressure is prevented from forming in the first storage part 21. This allows the operation of pushing down the rod 40 and the slider 30 to be performed easily.

Figure 10:
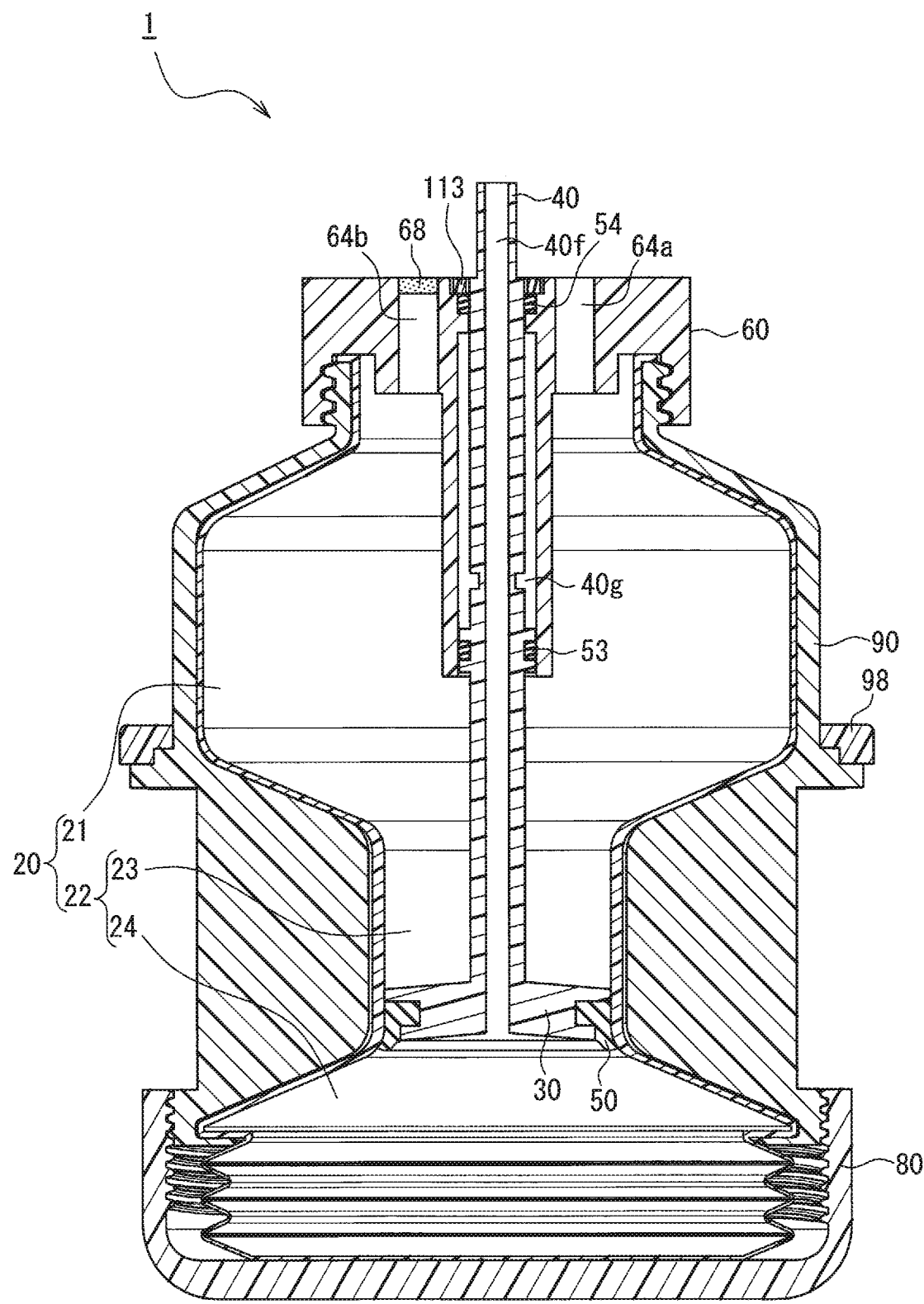
FIG. 10 is a cross sectional view of the device according to the first embodiment of the present invention in the state where recovery of a leukocyte component has been completed.

The descent of the slider 30 is stopped when all of the leukocyte component in the cylinder part 23 flows out of the storage vessel 20, thereby completing the recovery operation of the leukocyte component. FIG. 10 is a cross sectional view showing the device 1 in this state. The slider 30 has reached a lower opening (an opening on the auxiliary storage part 24 side) of the cylinder part 23 or in the vicinity thereof.

1.3. Action

As described above, the device 1 of the first embodiment includes the slider 30 movable in the storage vessel 20 from the first storage part 21 to the cylinder part 23 (the second storage part 22). When the slider 30 is in the first storage part 21, the first storage part 21 and the cylinder part 23 are in communication with each other. As the slider 30 enters the cylinder part 23, a liquid-tight seal is formed between the slider 30 and the inner peripheral surface of the cylinder part 23, and the slider 30 blocks the communication between the first storage part 21 and the cylinder part 23. The slider 30 can move in the cylinder part 23 while maintaining this liquid-tight seal. Thus, when blood is centrifugally separated while holding the slider 30 in the first storage part 21 and then the slider 30 is inserted into the cylinder part 23 from the first storage part 21, as the slider 30 enters the cylinder part 23, the blood component in the cylinder part 23 can be pushed out of the storage vessel 20 through the flow path 40*f*. When the blood is centrifugally separated such that the leukocyte component is present in the cylinder part 23 right before the insertion of the slider 30 into the cylinder part 23, the leukocyte component can be recovered through the flow path 40*f*.

The slider 30 slides on the inner peripheral surface in such a manner that the liquid-tight seal between the slider 30 and the inner peripheral surface of the cylinder part 23 is maintained. Thus, the leukocyte component attached to the cylinder part 23 is scraped (or scraped off) by sliding the slider 30. After the slider 30 has passed, almost no leukocyte component remains on the inner peripheral surface of the cylinder part 23. Therefore, the device 1 is advantageous in improving the recovery rate of the leukocyte component.

As described above, in the case of using a conventional device (see Patent Literature 1), a washing operation using physiological saline was needed for improving the recovery rate of the leukocyte component. However, there is a case that the leukocyte component attached to the inner peripheral surface of the storage vessel cannot be sufficiently recovered only by washing with physiological saline. On the other hand, because the slider 30 moves (i.e., slides) while being in contact with the cylinder part 30, the device 1 of the present embodiment can recover the leukocyte component attached to the inner peripheral surface of the cylinder part 23 more reliably. Therefore, in the present embodiment, the recovery rate of the leukocyte component is remarkably improved as compared to a conventional case.

Furthermore, in the case of using a conventional device, in addition to the step of washing the inside of the blood storage vessel with physiological saline, the step of subjecting the physiological saline containing the leukocyte component to centrifugal separation or the like to recover the leukocyte component from the physiological saline after the washing step is required. Thus, it takes a lot of time and effort to improve the recovery rate of the leukocyte component. On the other hand, in the case of using the device 1 of the present embodiment, the recovery rate of the leukocyte component can be improved without performing the washing step and the centrifugal separation step with the physiological saline. Therefore, use of the device 1 allows the leukocyte component to be recovered efficiently.

The conventional device is required to be provided with two blocking members movable in the storage vessel for closing the upper and lower openings of the third storage part (corresponding to the cylinder part 23 of the first embodiment) of the storage vessel. In addition, because the leukocyte component in the third storage part is sucked by the syringe in the state where the upper and lower openings of the third storage part of the storage vessel are closed, in addition to the flow path for allowing the leukocyte component to flow out of third storage part, the conventional device is required to be provided with an air flow path for allowing the air to flow into the third storage part in accordance with the outflow of the leukocyte component so that a negative pressure is not caused in the third storage part. In contrast, in the present embodiment, only the slider 30 is movable in the storage vessel 20. In addition, because the leukocyte component in the second storage part 22 is extruded by the slider 30 to recover, the air flow path leading to the second storage part 22 is unnecessary. Furthermore, the flow path 40*f* for allowing the leukocyte component to flow out is provided in the rod 40 for moving the slider 30. As a result, the device 1 of the first embodiment has a structure remarkably simpler than the conventional device.

In the conventional device, in the state where the upper and lower openings of the third storage part (corresponding to the cylinder part 23 of the first embodiment) of the storage vessel are closed with two blocking members, the leukocyte component in the third storage part is recovered through a flow path provided in the rod that holds the blocking member (first blocking member) for closing the lower opening of the third storage part. Because the conventional device is configured so that air flows into the third storage part as the leukocyte component is recovered from the third storage part, the flow path through which the leukocyte component flows is in communication with the third storage part through an opening provided in the vicinity of the first blocking member positioned at the lower end of the third storage part. Because this elongates the flow path, the amount of the leukocyte component attached to the inner wall surface of the flow path increases. The leukocyte component is also attached to the surface of the lower first blocking member. In this manner, because the region to which the leukocyte component is attached is wide, there has been a problem in that the leukocyte component cannot be recovered sufficiently. On the other hand, in the present embodiment, because the flow path 40*f* for recovering the leukocyte component is provided on the rod 40 that holds the slider 30, the length of the flow path 40*f* can be made shorter than the flow path of the conventional device. Furthermore, the device of the present embodiment does not include a member corresponding to the first blocking member of the conventional device. Thus, in the present embodiment, the region to which the leukocyte component is attached is relatively small. Therefore, the device 1 of the present embodiment is advantageous in improving the recovery rate of the leukocyte component.

In the conventional device, after closing the upper and lower openings of the third storage part (corresponding to the cylinder part of the first embodiment) of the storage vessel sequentially with the blocking members, the leukocyte component in the third storage part is recovered. At the time of closing the lower opening of the third storage part with the blocking member, there may be a case in which the blocking member perturbs the boundary between a leukocyte component layer and an erythrocyte component layer, which causes mixing of the leukocyte component and the erythrocyte component in the vicinity of the boundary. As a result, a problem such as mixing of the erythrocyte component into the leukocyte component or failing in recovering all of the leukocyte component sometimes raised. On the other hand, in the first embodiment, there is no need to close the lower opening (the opening on the auxiliary storage part 24 side) of the cylinder part 23. Even when the slider 30 is inserted into the cylinder part 23 from the upper opening, the boundary between the leukocyte component layer and the erythrocyte component layer, which is in the vicinity of the lower opening of the cylinder part 23, is hardly affected. Thus, the above-described problem of the conventional device is solved. Also from this point, the device 1 is advantageous in improving the recovery rate of the leukocyte component.

Furthermore, in the first embodiment, for recovering the leukocyte component, it is only required to push down the rod 40 to move the slider 30 from the first storage part 21 to the cylinder part 23 after the centrifugal separation. The principle of pushing the rod 40 to push out the leukocyte component is basically the same as the principle of pushing a plunger into the outer cylinder part to push out the liquid in the outer cylinder part in a common syringe. Because the leukocyte component can be recovered simply by moving the rod 40 and the slider 30 downward, the possibility of erroneous operation is low and the burden on an operator can be reduced.

1.4. Blood Component Recovery Device

A blood component recovery device suitable for recovering the leukocyte component using the device 1 of the first embodiment is described.

Figure 11:
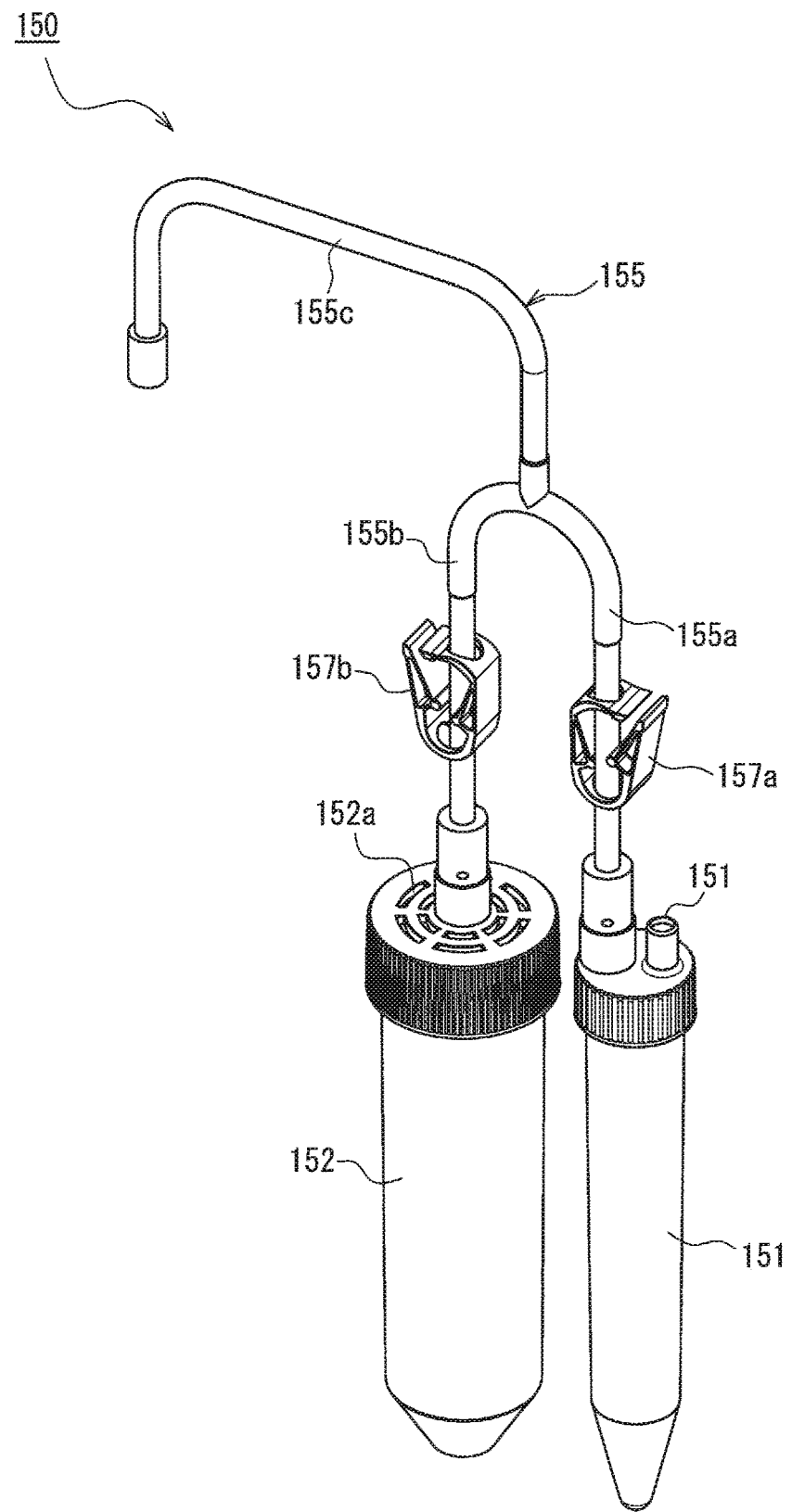
FIG. 11 is a perspective view showing a blood component recovery device according to one embodiment of the present invention.

FIG. 11 shows an example of a blood component recovery device 150. The recovery device 150 includes a first container 151, a second container 152, and a flexible transparent tube 155. The tube 155 branches into a Y shape (or T shape) from a main tube 155*c* to two branch tubes 155*a* and 155*b*. The main tube 155*c* is connected to the upper end of the rod 40 of the device 1 (see FIGS. 1 and 2). The branch tubes 155*a* and 155*b* are connected to the containers 151 and 152, respectively. Clamps 157*a* and 157*b* for opening and closing the respective flow paths are provided on the branch tubes 155*a* and 155*b*. Vent holes 151*a* and 152*a* for allowing gas communication between the inside and the outside of the containers 151 and 152 are provided in the caps of the containers 151 and 152. Vent filters (not shown) that allow gas but not liquid to pass are provided on the vent holes 151*a* and 152*a*.

Recovery of the blood component using the recovery device 150 is performed as described below.

After subjecting the blood in the device 1 to centrifugal separation, the main tube 155*c* is connected to the upper end of the rod 40 in the initial state where the slider 30 is in the initial position (see FIG. 2). Thereafter, the rod 40 is descended, and the slider 30 is fitted into the upper opening of the cylinder part 23 (see FIG. 9).

The blood component in the cylinder part 23 is observed through the support member 90 and the storage vessel 20. For example, when a thin blood plasma component layer is present right under the slider 30 and a leukocyte component layer is present under the thin blood plasma component layer in the cylinder part 23, the clamp 157*a* is opened and the clamp 157*b* is closed. Then, the rod 40 is descended. As the slider 30 descends in the cylinder part 23, the blood plasma component flows out first and then the leukocyte component subsequently flows out from the cylinder part 23 through the flow path 40*f* of the rod 40 and the tube 155. The blood component flowing through the tube 155 is observed through the tube 155. When the blood component flowing through the tube 155 is switched from the blood plasma component to the leukocyte component, the clamp 157*a* is closed and the clamp 157*b* is opened. Thereafter, the rod 40 is subsequently descended. Thereafter, when the blood component flowing through the tube 155 is switched from the leukocyte component to the erythrocyte component (see FIG. 10), the clamp 157b is closed and the operation of descending the rod 40 is stopped. Thus, the first container 151 can recover the blood plasma component and the second container 152 can recover the leukocyte component.

As described above, the recovery device 150 includes the two containers 151 and 152 and a switching mechanism (the clamps 157a and 157b) for switching the communication between the two containers 151 and 152 and the flow path 40f of the device 1. Use of such a recovery device 150 allows a leukocyte component of high purity in which a blood plasma component and an erythrocyte component are substantially not mixed to be recovered by switching the communication between the containers 151 and 152 and the flow path 40f by the switching mechanism (the clamps 157a and 157b) even when the blood plasma component layer is present beneath the slider 30 or the erythrocyte component layer enters beneath the lower part of the cylinder part 23 at the time of fitting the slider 30 into the upper opening of the cylinder part 23 (see FIG. 9).

Thus, when the recovery device 150 is used, the upper end and the lower end of the leukocyte component layer are not required to exactly coincide with the upper end and the lower end of the cylinder part 23 in the state where the slider 30 after the centrifugal separation is in the initial position (see FIG. 2). The blood plasma component layer and the erythrocyte component layer may enter the cylinder part 23 as long as the entire leukocyte component layer is present in the cylinder part 23. This makes it possible to omit the step of calculating the amounts of the erythrocyte component and the blood plasma of the collected blood and to ease the adjustment accuracy of the compressive deformation amount of the bellows structure 28, which allows the recovery operation of the leukocyte component to be simplified. Furthermore, by omitting the volume adjusting mechanism such as the bellows structure 28, the structures of the storage vessel 20 and the device 1 can be further simplified.

The recovery device 150 includes the clamps 157a and 157b as a switching mechanism selectively communicating the flow path 40f with either the first container 151 or the second container 152. The structure of the switching mechanism, however, is not limited thereto. For example, instead of the clamps 157a and 157b, the switching mechanism may be a three-way stopcock provided in a Y-shaped (or T-shaped) branch part of the tube 155.

The structures of the first container 151 and the second container 152 are not limited to the above-described embodiment. For example, the first container 151 and/or the second container 152 may be a bag obtained by bonding flexible sheets. In this case, the vent holes 151a and 152a may not be provided in the bag.

2. Second Embodiment

The second embodiment of the present invention is described. In the drawings to be referred to in the description below, members or elements having the same functions as the members or elements shown in the drawings referred to in the first embodiment are given the same reference signs as in the first embodiment. In the second embodiment, a redundant description of these members or elements is omitted. Therefore, the reference shall be made to the description of the first embodiment as necessary. Hereinafter, the second embodiment is described focusing on differences between the first embodiment and the second embodiment.

2.1. Structure of Blood Component Separator

The structure of a blood component separator (hereinafter, simply referred to as a "device") 2 according to the second embodiment of the present invention is described below.

Figure 12:
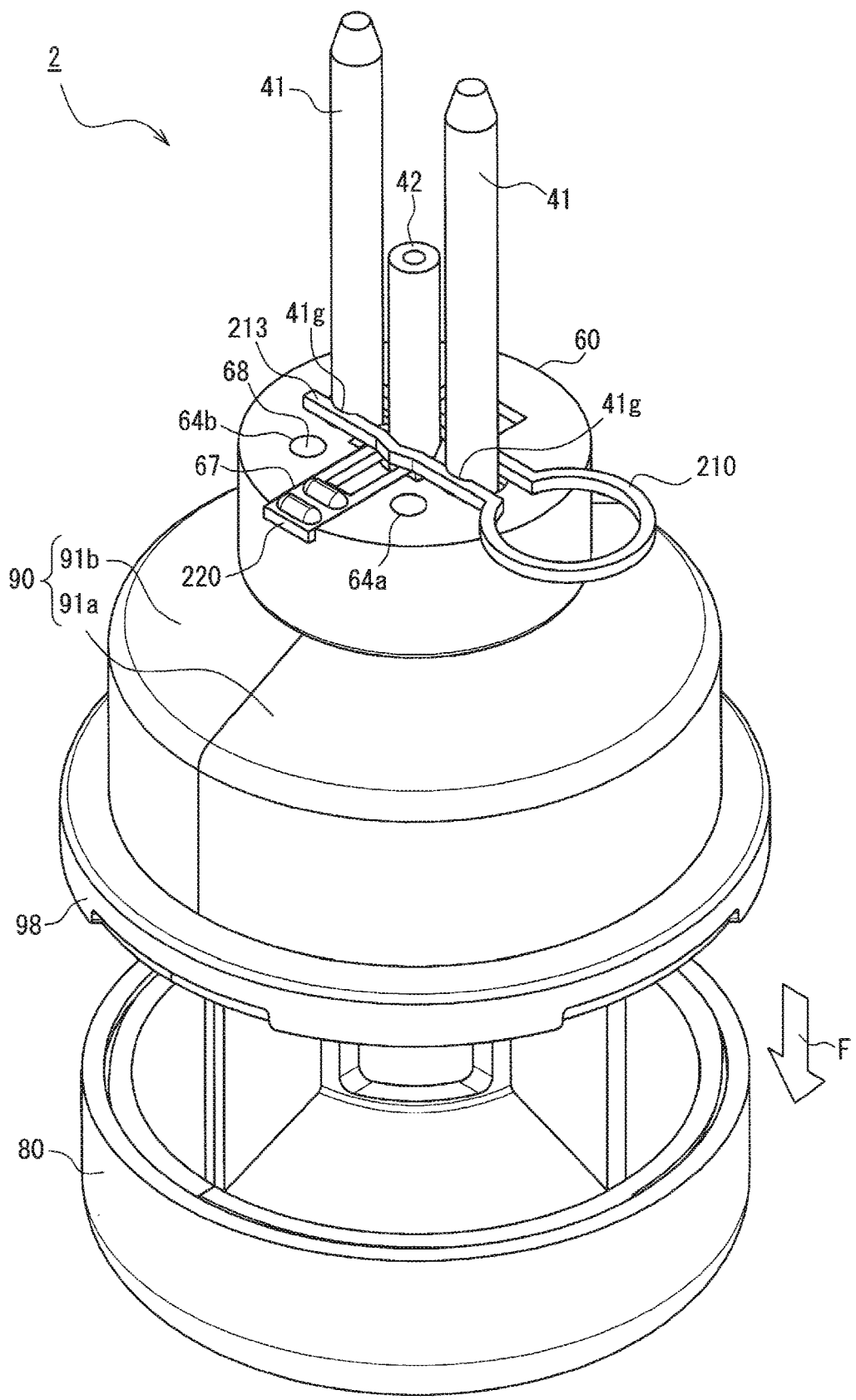
FIG. 12 is a perspective view of a blood component separator according to the second embodiment of the present invention.
Figure 13:
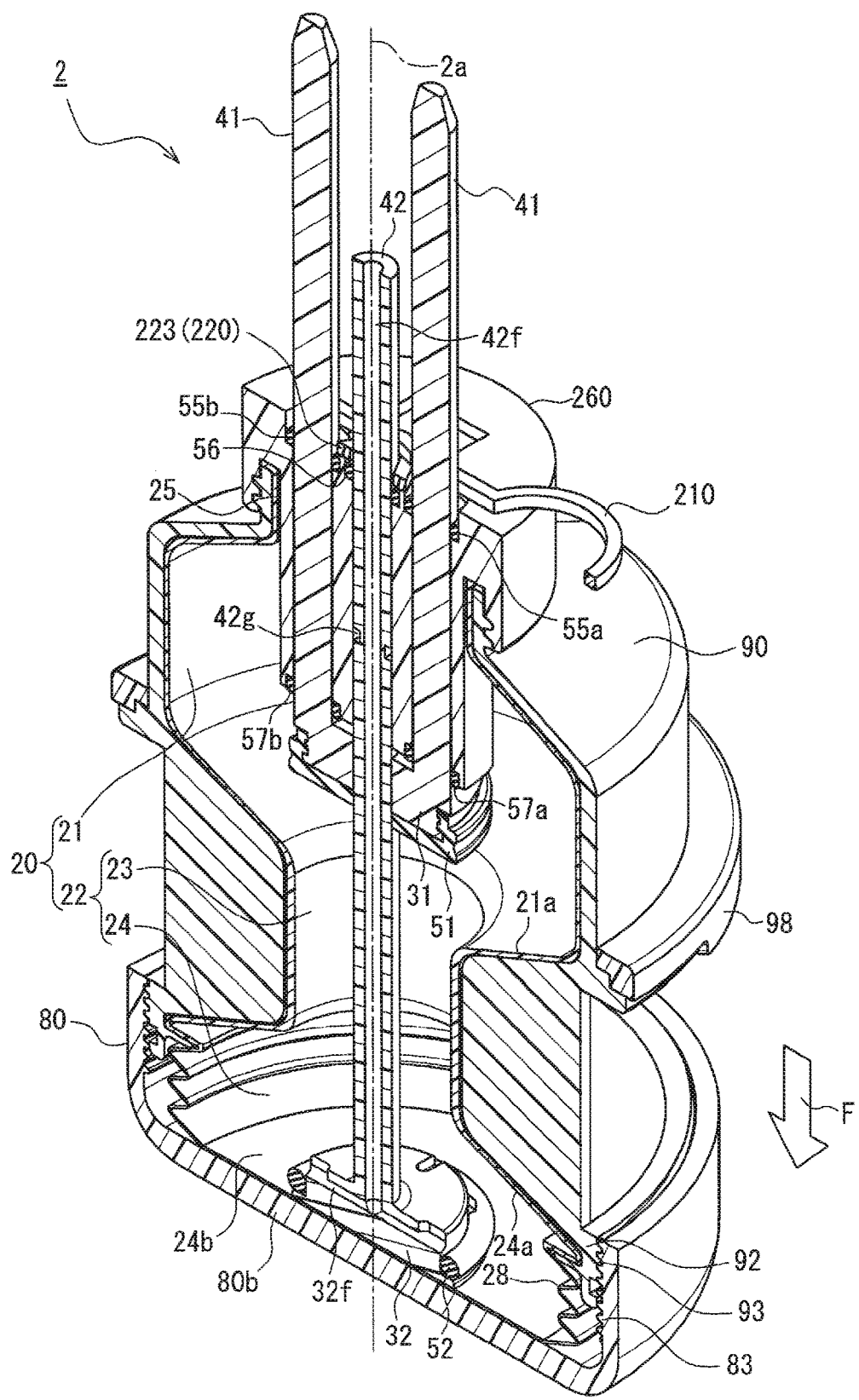
FIG. 13 is a cross sectional perspective view of the device according to the second embodiment of the present invention.
Figure 14:
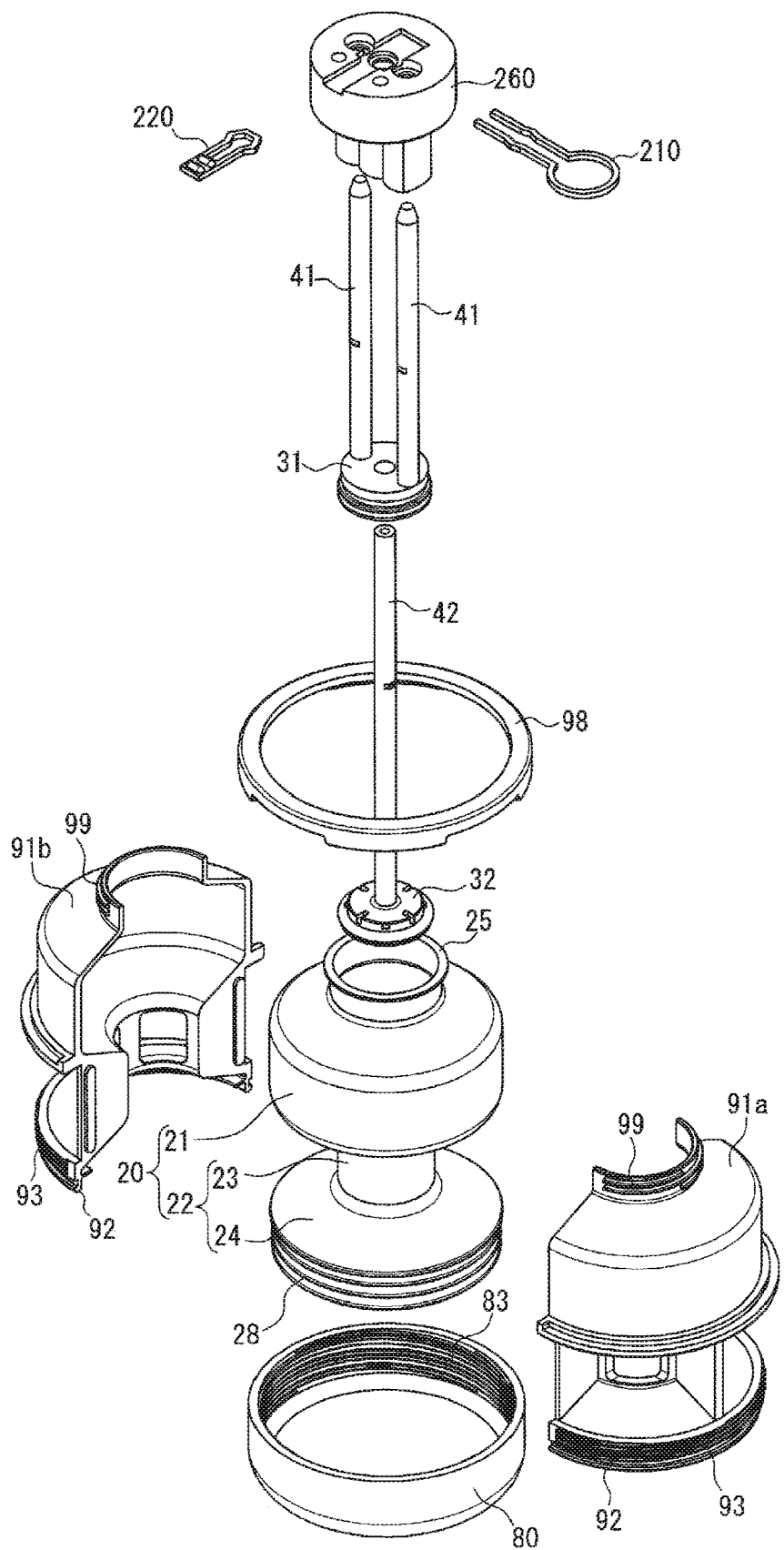
FIG. 14 is an exploded perspective view of the device according to the second embodiment of the present invention.

FIG. 12 is a perspective view of the device 2. FIG. 13 is a cross sectional perspective view taken along the vertical direction surface of the device 2. In FIG. 13, a dashed-dotted line 2a is the central axis of the device 2. FIG. 14 is an exploded perspective view of the device 2.

As shown in FIG. 13, the device 2 includes a slider 31 in a first storage part 21 and a blocking member 32 in an auxiliary storage part 24. The slider 31 functions as the slider 30 of the first embodiment and is held at the lower end of two first rods 41. The blocking member 32 is held at the lower end of the second rod 42.

Figure 15A:
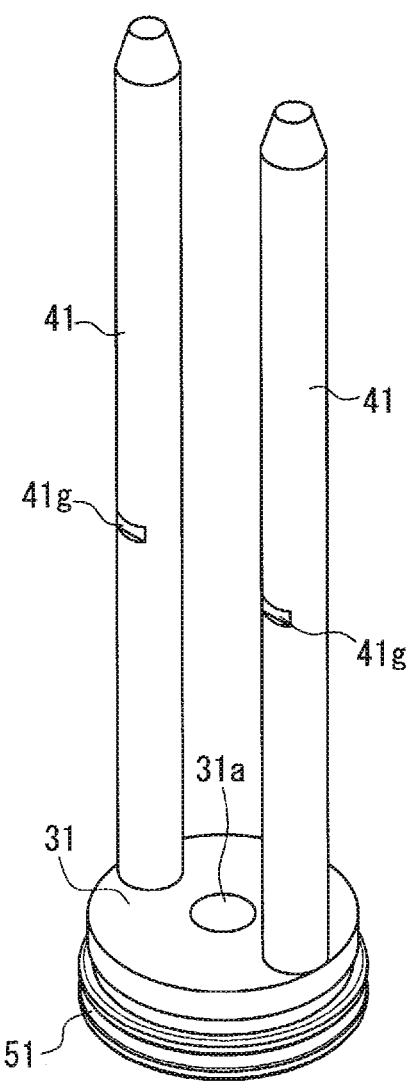
FIG. 15A is a perspective view showing a slider and a first rod in the second embodiment of the present invention.
Figure 15B:
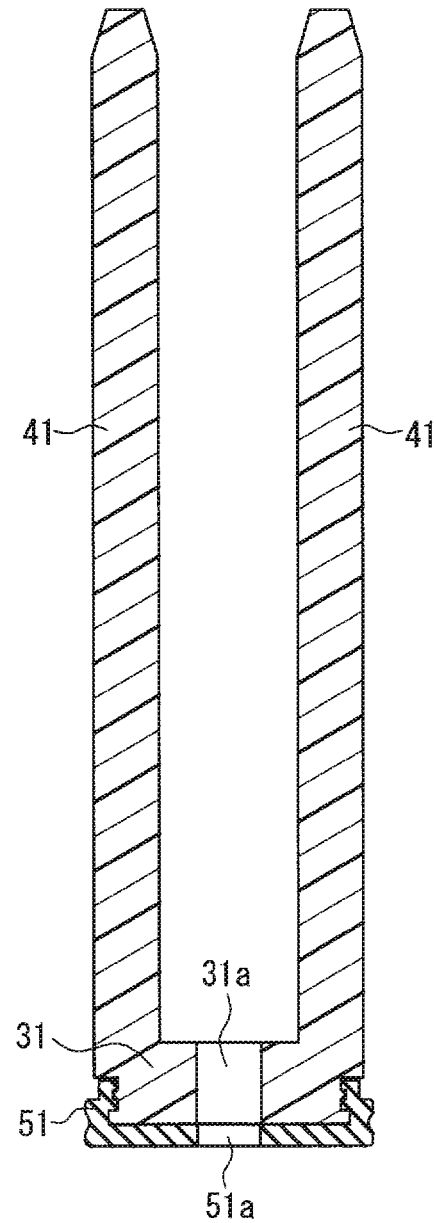
FIG. 15B is a cross sectional view of FIG. 15A.

FIG. 15A is a perspective view of the slider 31 and the first rods 41, and FIG. 15B is a cross sectional view thereof. The slider 31 has a substantially disc shape (or a thin substantially cylindrical shape). The slider 31 is provided with a through hole 31a penetrating the slider 31 in the vertical direction at the center thereof. A gasket 51 having a bottomed cylindrical shape is attached to the slider 31 so as to cover the outer peripheral surface and the lower surface of the slider 31. A through hole 51a penetrating the bottom plate of the gasket 51 in the vertical direction is formed at a position corresponding to the through hole 31a of the slider 31. The opening diameter of the through hole 51a is preferably slightly smaller than the opening diameter of the through hole 31a.

The first rod 41 is a solid bar-like member. The two first rods 41 are provided at positions symmetrical with respect to the through hole 31a on the upper surface of the slider 31. The two first rods 41 extend upward in parallel to each other.

On the outer peripheral surface of each first rod 41, a pair of first locking grooves 41g extending in the horizontal direction are formed (in FIG. 15A, the first locking groove 41g provided on the rear side of each first rod 41 cannot be seen). It is to be noted that the first locking groove 41g provided on each of the first rods 41 is not necessarily divided in the circumferential direction, and may be an annular groove continuous in the circumferential direction, for example.

In the present embodiment, the slider 31 (excluding the gasket 51) and the first rods 41 are integrally produced as a single piece as a whole. The present invention, however, is not limited thereto, and the separately prepared slider 31 and the first rods 41 may be combined.

Figure 16A:
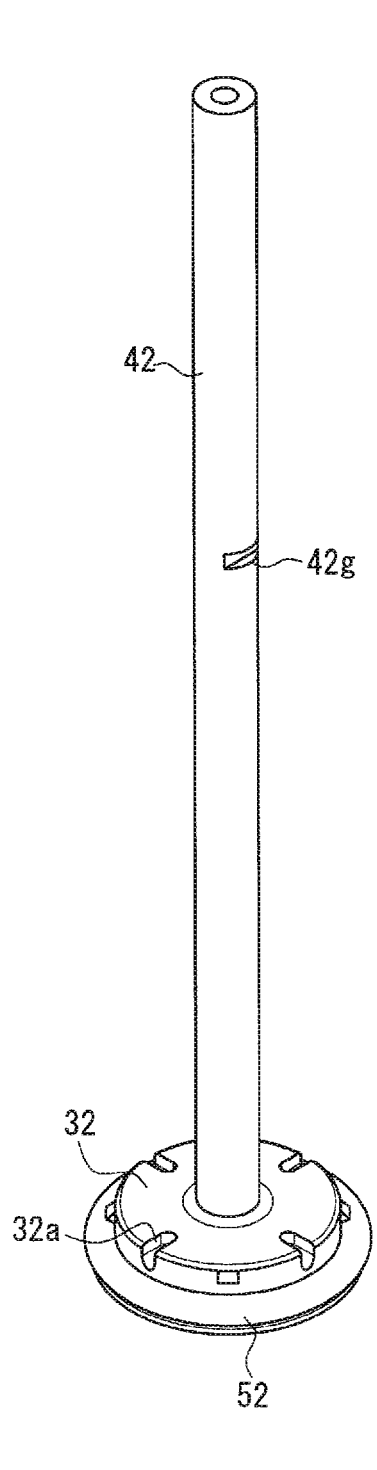
FIG. 16A is a perspective view showing a blocking member and a second rod in the second embodiment of the present invention.
Figure 16B:
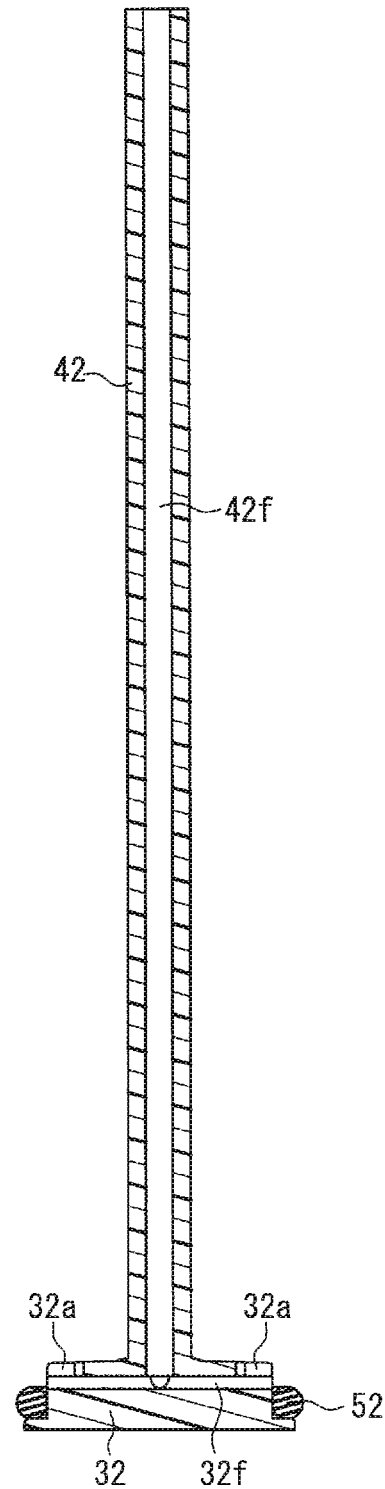
FIG. 16B is a cross sectional view of FIG. 16A.

FIG. 16A is a perspective view of the blocking member 32 and the second rod 42, and FIG. 16B is a cross sectional view thereof. The blocking member 32 has a substantially disk shape (or a thin substantially cylindrical shape). An O ring 52 is attached to the cylindrical outer peripheral surface of the blocking member 32. Four openings 32a are formed in the upper surface of the blocking member 32. The four openings 32a are in communication with one another through a flow path 32f having a substantially cross-shape in plan view formed in the blocking member 32. The number of the openings 32a is not limited to four, and may be more than four or less than four.

The second rod 42 is a bar-like member having a hollow cylindrical shape. The second rod 42 preferably has the same outer diameter as the first rod 41 (see FIG. 15A). The second rod 42 is provided at the center of the upper surface of the blocking member 32. As shown in FIG. 16B, the flow path 42f in the second rod 42 and the flow path 32f in the blocking member 32 are in communication with each other. Thus, the opening 32a, the flow path 32f, and the flow path 42f are sequentially in communication.

The opening 32a and the flow path 32f of the blocking member 32 may be omitted and a lateral hole extending along the radial direction and in communication with the flow path 42f may be provided in the second rod 42 in the vicinity of the blocking member 32.

On the outer peripheral surface of the second rod 42, a pair of second locking grooves 42g extending in the horizontal direction are formed (in FIG. 16A, the second locking groove 42g provided on the rear side of each second rod 42 cannot be seen). It is to be noted that, the second locking groove 42g is not necessarily divided in the circumferential direction, and may be an annular groove continuous in the circumferential direction, for example.

Figure 17A:
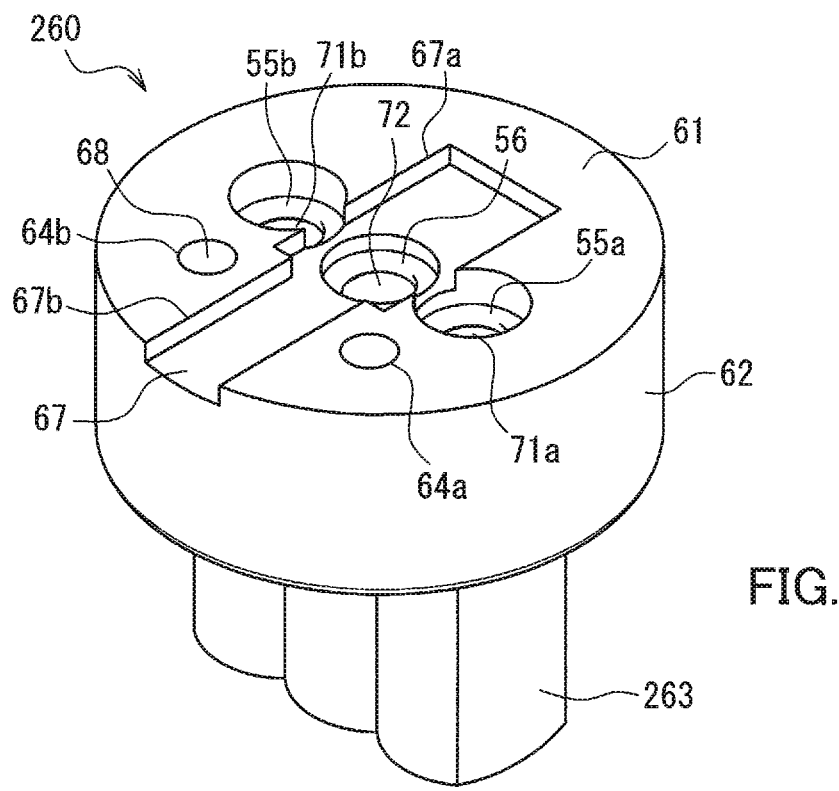
FIG. 17A is a perspective view showing a top cap in the second embodiment of the present invention.
Figure 17B:
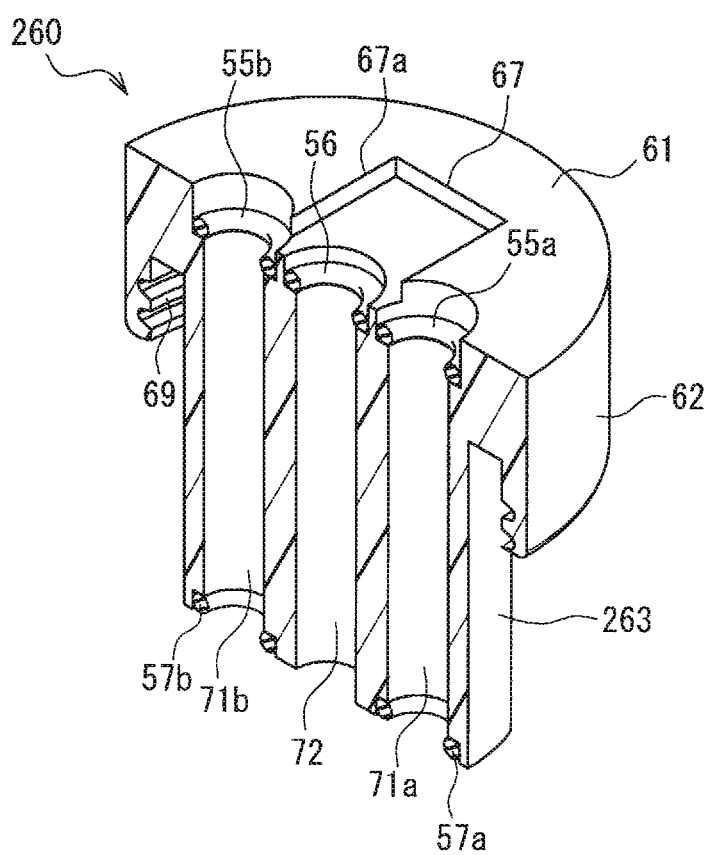
FIG. 17B is a cross sectional perspective view of FIG. 17A.

FIG. 17A is a perspective view of a top cap 260, and FIG. 17B is cross sectional perspective view thereof. The top cap 260 includes a circular top plate 61, a cylindrical outer peripheral wall 62 extending downward from the outer peripheral edge of the top plate 61, and a guide tube 263 extending downward from the lower surface of the top plate 61.

A groove 67 extending straight is provided on the upper surface of the top plate 61. The width of the groove 67 is not constant, and, similar to the groove 65 of the first embodiment (see FIG. 5A), the groove 67 includes a wide part 67a having a relatively wide width and a narrow part 67b having a relatively narrow width. The wide part 67a is provided at the center of the top plate 61 and the narrow part 67b connects the wide part 67a and the outer peripheral edge of the top plate 61.

Three guide holes 71a, 71b, and 72 penetrate the top plate 61 and the guide tube 263 in the vertical direction. The guide holes 71a, 71b, and 72 are arranged along a straight line substantially orthogonal to the longitudinal direction of the groove 67. The first guide holes 71a and 71b are provided on both sides of the groove 67, and the second guide hole 72 is provided coaxially with the top plate 61 in the wide part 67a of the groove 67. The edge of the opening of each of the guide holes 71a, 71b, and 72 facing upward is slightly expanded, which forms an annular dent. O rings 55a, 55b, and 56 are attached to the insides of the dents of the guide holes 71a, 71b, and 72, respectively. Similarly, the edge of the opening of each of the guide holes 71a and 71b facing downward is slightly expanded, which forms an annular dent. O rings 57a and 57b are attached to the insides of the dents of the guide holes 71a and 71b, respectively.

Two through holes 64a and 64b penetrating the top plate 61 in the vertical direction are provided in the top plate 61 in a region where the groove 67 is not formed. As in the first embodiment, the through hole 64a is used as an injection port and the through hole 64b is used as a vent port.

Figure 18:
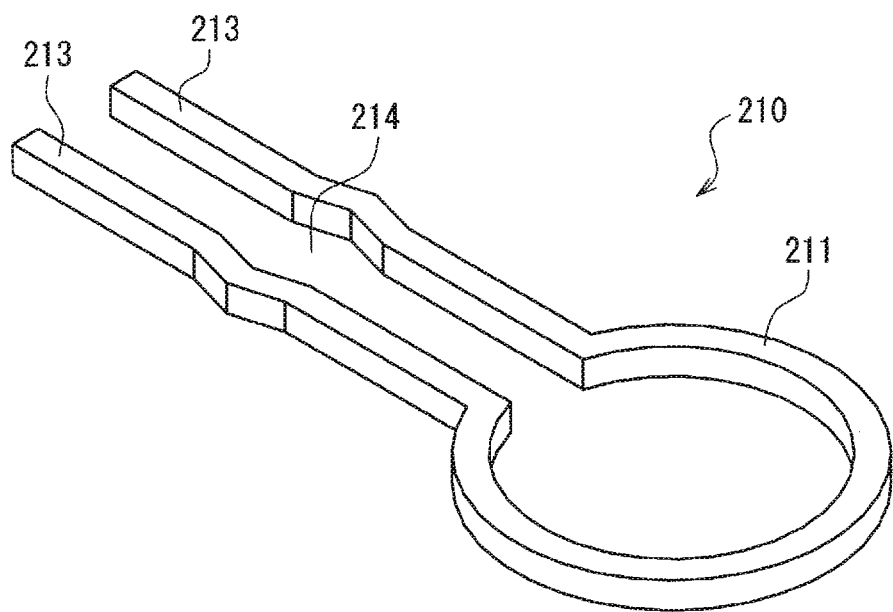
FIG. 18 is a perspective view showing a first locking member in the second embodiment of the present invention.

FIG. 18 is a perspective view of a first locking member 210. The first locking member 210 includes a substantially "C"-shaped operation part 211 and two locking bars 213 extending from both ends of the operation part 211. The two locking bars 213 extend in parallel to each other except for a widened part 214 provided at a substantially middle position in the longitudinal direction thereof. The distance between the locking bars 213 at the widened part 214 is wider than the distance between the locking bars 213 at the other part. The inner diameter of the widened part 214 (the diameter of the inscribed circle of the widened part 214) is substantially equal to or slightly larger than the outer diameter of the second rod 42 (see FIG. 16A). The distance between two locking bars 213 excluding the widened part 214 is smaller than the outer diameter of the first rod 41 (see FIGS. 15A and 15B). As described below, the part of the two locking bars 213 at the part excluding the widened part 214 is configured to be engageable with the first locking groove 41g (see FIG. 15A) formed on each first rod 41.

Figure 19:
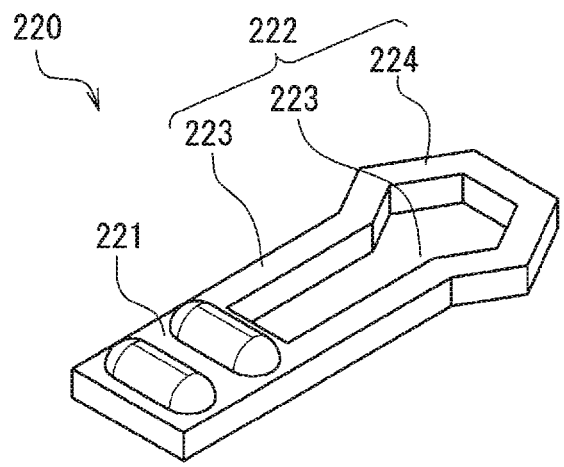
FIG. 19 is a perspective view showing a second locking member in the second embodiment of the present invention.

FIG. 19 is a perspective view of a second locking member 220. Similar to the locking member 110 of the first embodiment (see FIG. 6), the second locking member 220 includes a substantially rectangular thin plate-like operation part 221 and a substantially "U"-shaped frame 222. The frame 222 includes a diameter-enlarged part 224 and two locking bars 223 parallel to each other between the diameter-enlarged part 224 and the operation part 221. While the diameter-enlarged part 224 has a substantially regular hexagonal shape in the present embodiment, the shape of the diameter-enlarged part 224 is not limited thereto, and the diameter-enlarged part 224 may have any shape such as a circular shape (see FIG. 6), an elliptical shape, a regular octagonal shape, or the like. The inner diameter of the diameter-enlarged part 224 (the diameter of the inscribed circle of the diameter-enlarged part 224) is substantially equal to or slightly larger than the outer diameter of the second rod 42 (see FIG. 16A). The outside dimension of the diameter-enlarged part 224 is larger than the outside dimension of the two locking bars 223. The distance between the two locking bars 223 is smaller than the inner diameter of the diameter-enlarged part 224 and smaller than the outer diameter of the second rod 42. As described below, the two locking bars 223 are configured to be engageable with the second locking groove 42g formed on the second rod 42 (see FIG. 16A).

As can be understood from FIGS. 13 and 14, the slider 31 held by the first rod 41, the blocking member 32 held by the second rod 42, and the top cap 260 are, in summary, attached to the storage vessel 20 as described below.

The support member 90 is attached to the storage vessel 20. The blocking member 32 is inserted into the storage vessel 20 from the opening 25. Using the second rod 42, the blocking member 32 is moved into the auxiliary storage part 24 from the first storage part 21 through the cylinder part 23. The second rod 42 is sequentially inserted into the through hole 51a of the gasket 51 and the through hole 31a of the slider 31. Furthermore, the second rod 41 is inserted into the second guide hole 72 of the top cap 260 from below. Moreover, two first rods 41 are inserted into the first guide holes 71a and 71b of the top cap 260 from below. The top cap 260 is screwed to the upper end of the support member 90. The opening 25 is covered with the top plate 61. The rods 41, 41, and 42 penetrate the top cap 260 and project upward.

The second rod 42 is inserted into the diameter-enlarged part 224 of the second locking member 220. Then, the second locking member 220 is fitted into the groove 67 formed on the upper surface of the top cap 260. More specifically, the diameter-enlarged part 224 and the operation part 221 of the second locking member 220 are fitted into the wide part 67a and the narrow part 67b of the groove 67, respectively (see FIG. 20).

Subsequently, the rods 41, 41, and 42 are inserted into the space between the two locking bars 213 of the first locking member 210. The position of the first locking member 210 in the horizontal direction is adjusted so that the second rod 42 is positioned in the widened part 214. Then, the locking bar 213 is fitted into the first locking groove 41g provided on the first rod 41. The first locking member 210 is placed on the top plate 61 of the top cap 260.

Figure 20:
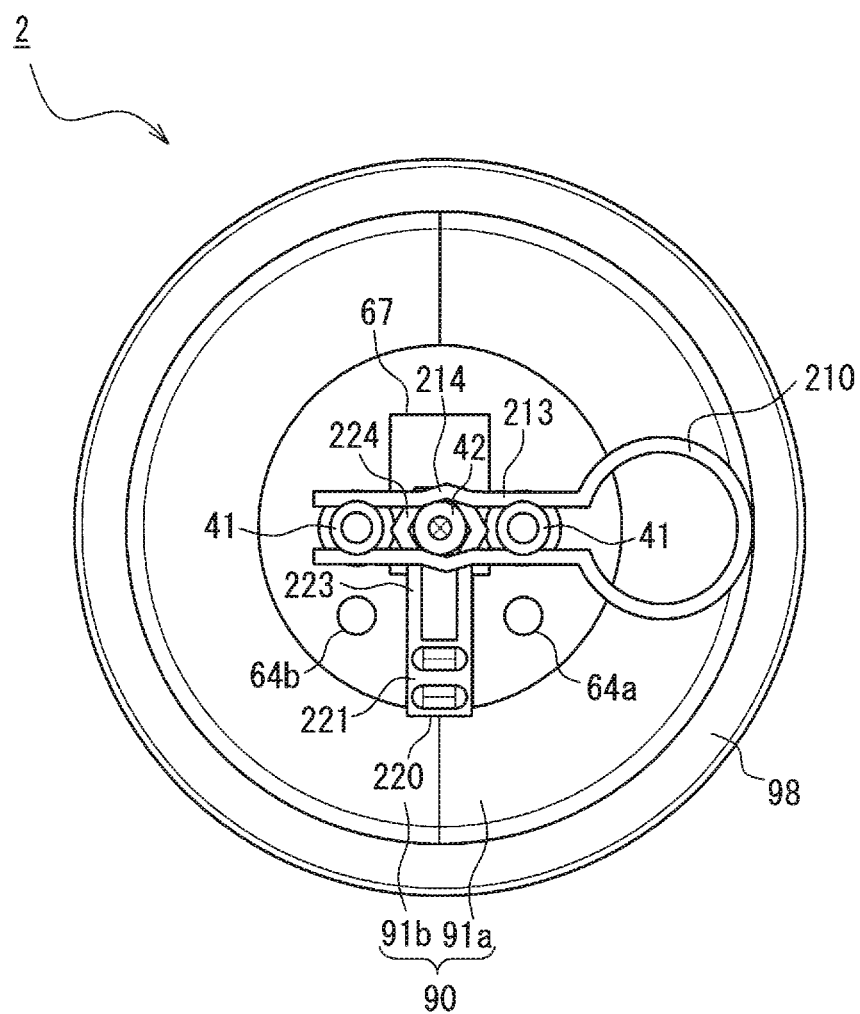
FIG. 20 is a plan view of the device according to the second embodiment of the present invention in the initial state.

FIG. 20 is a plan view of the device 2 assembled in this manner. The second rod 42 is positioned in the diameter-enlarged part 224 of the second locking member 220 and in the widened part 214 of the first locking member 210. The first rod 41 is positioned between the locking bars 213 of the first locking member 210. FIGS. 12 and 13 show the device 2 in which the first and second locking members 210 and 220 are in the position of FIG. 20.

As shown in FIG. 12, the locking bar 213 (excluding the widened part 214) of the first locking member 210 is engaged with the first locking groove 41g of the first rod 41. This prevents the first rod 41 and the slider 31 held by the first rod 41 from descending (see FIG. 13). In this manner, the first locking member 210 and the first locking groove 41g provided on the first rod 41 to be engaged with the first locking member 210 configure a "locking mechanism for slider 31" (hereinafter, referred to as a "first locking mechanism") that prevents the slider 31 from descending. Switching between activation and invalidation of the lock by the first locking mechanism can be achieved by attaching and detaching the first locking member 210 to the first rod 41. When the first rod 41 is positioned between the locking bars 213 and the locking bar 213 is engaged with the first locking groove 41g as shown in FIG. 20, the first locking mechanism is in the locked state. When the first locking member 210 is taken out of the first rod 41 (see FIG. 22 described below), the first locking mechanism is in the unlocked state. The first locking member 210 can be taken out of the first rod 41 by inserting a finger into the operation part 211 and pulling the first locking member 210 in the arrangement direction of the rods 41, 42, and 41.

When the first locking mechanism is in the locked state, as shown in FIG. 13, the slider 31 held at the lower end of the first rod 41 floats in the air in the first storage part 21 without contacting with the inner peripheral surface of the first storage part 21. The position of the slider 31 shown in FIG. 13 is referred to as the "initial position" of the slider 31.

Unless the engagement (locked state) between the first locking member 210 (locking bar 213) and the first rod 41 is released, even if a downward force is applied to the first rod 41 or gravity or a centrifugal force acts on the first rod 41 and the slider 31, the slider 31 does not descend from the initial position. The first locking mechanism is advantageous for stably holding the slider 31 in the initial position. Thus, the communication between the first storage part 21 and the second storage part 22 (the cylinder part 23) is ensured. This is advantageous for a reliable blood flowing from the first storage part 21 to the second storage part 22 when blood is injected from the opening 25 of the storage vessel 20. In addition, such a structure is advantageous for centrifugal separation of blood into a blood plasma component to be stored in the first storage part 21, a leukocyte component to be stored in the cylinder part 23, and an erythrocyte component to be stored in the auxiliary storage part 24.

As shown in FIG. 20, the inner diameter of the diameter-enlarged part 224 of the second locking member 220 is equal to or larger than the outer diameter of the second rod 42. The inner diameter of the widened part 214 of the first locking member 210 is equal to or larger than the outer diameter of the second rod 42. Thus, in FIG. 13, the second rod 42 and the blocking member 32 held at the lower end of the second rod 42 are movable in the vertical direction with respect to the storage vessel 20.

Figure 21A:
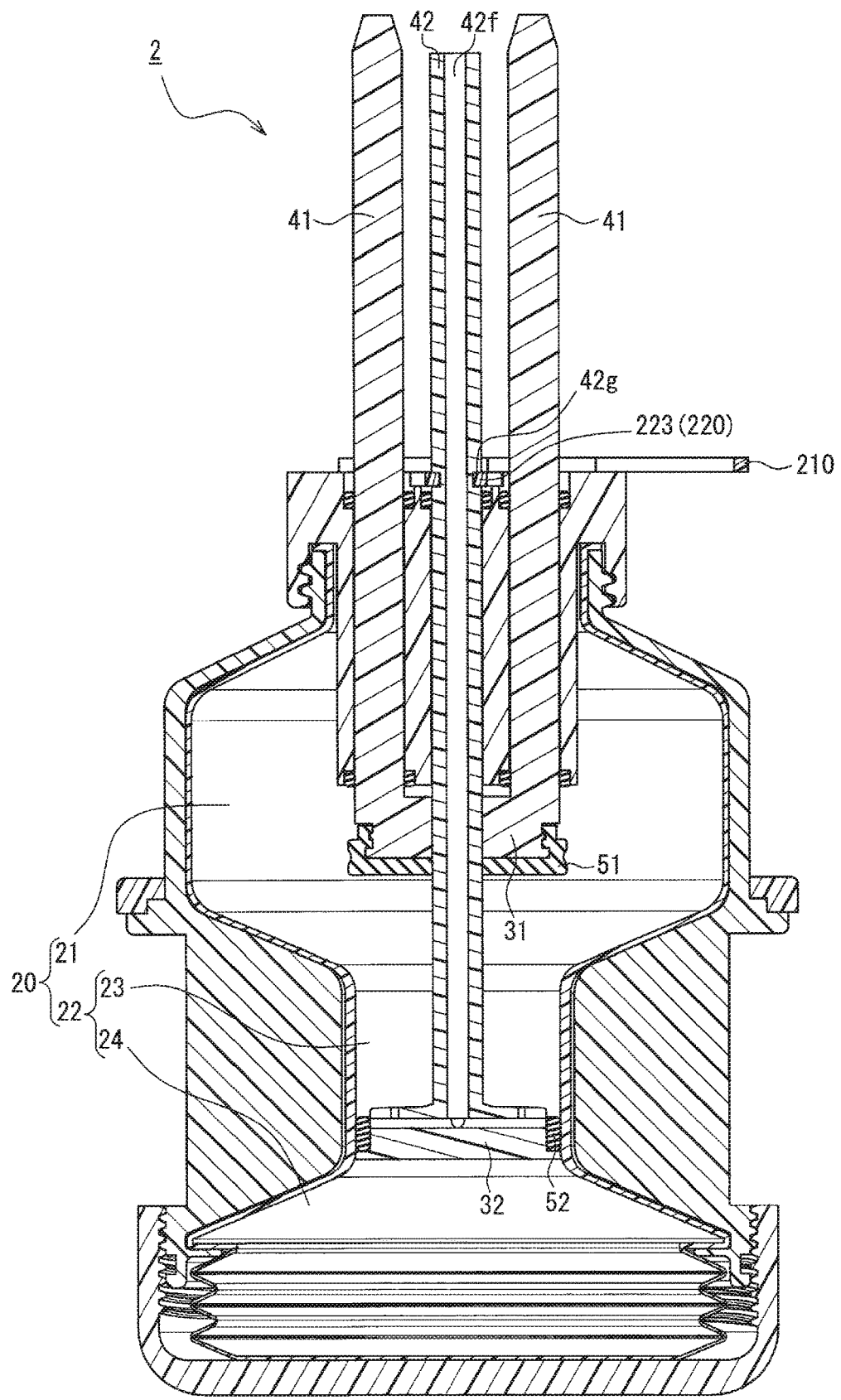
FIG. 21A is a cross sectional view showing a device according to the second embodiment of the present invention in the state where communication between a slider and an auxiliary storage part is blocked with a blocking member.

On the other hand, when the second rod 42 is raised so that the second locking groove 42g is positioned at the same level as the second locking member 220, the locking bar 223 of the second locking member 220 can be fitted into the second locking groove 42g of the second rod 42 (see FIGS. 21A and 21B described below).

When the locking bar 223 is engaged with the second locking groove 42g, the second rod 42 and the blocking member 32 held by the e second rod 42 are prevented from descending. In this manner, the second locking member 220 and the second locking groove 42g provided on the second rod 42 to be engaged with the second locking member 220 configure a "locking mechanism for blocking member 32" (hereinafter, referred to as a "second locking mechanism") that prevents the blocking member 32 from descending. Switching between activation and invalidation of the lock by the second locking mechanism can be achieved by moving the second locking member 220 in the groove 67 in the horizontal direction. When the second rod 42 is positioned in the diameter-enlarged part 224 as shown in FIG. 20, the second locking mechanism is in the unlocked state. When the second rod 42 is positioned between the locking bars 223 and the locking bar 223 is engaged with the second locking groove 42g (see FIGS. 21A and 21B described below), the second locking mechanism is in the locked state. The second locking member 220 can be moved by pressing a finger against the operation part 221.

In FIG. 13, the blocking member 32 is in contact with the bottom plate 24b of the auxiliary storage part 24. The position of the blocking member 32 shown in FIG. 13 is referred to as the "initial position" of the blocking member 32.

In the present invention, the state where the slider 31 and the blocking member 32 are both in the initial position, the first locking member 210 and the first rod 41 are engaged (locked state), and the second locking member 220 and the second rod 42 are not engaged (unlocked state) is referred to as the "initial state" (FIGS. 12, 13, and 20).

A liquid-tight seal is formed between the outer peripheral surface of the first rod 41 and the O rings 55a, 55b, 57a, and 57b held by the top cap 260, and a liquid-tight seal is formed between the outer peripheral surface of the second rod 42 and the gasket 51 provided on the slider 31 and the O ring 56 held by the top cap 260. Furthermore, the top cap 260 liquid-tightly seals the opening 25 at the upper end of the storage vessel 20. Accordingly, the space in the storage vessel 20 excluding the flow paths 32f and 42f and the through holes 64a and 64b of the top cap 260 (see FIG. 17A) is liquid-tightly sealed.

The material of the slider 31 and the blocking member 32 is preferably a hard material that can be substantially regarded as a rigid body so that the gasket 51 and the O ring 52 can form a liquid-tight seal with the inner peripheral surface of the cylinder part 23 (details are described below). Regarding the material of the slider 31 and the blocking member 32, reference can be made to the description as to the slider 30 of the first embodiment.

Regarding the material of the gasket 51 and the O rings 52, 55a, 55b, 56, 57a, and 57b, reference can be made to the description as to the gasket 50 and the O rings 53 and 54 of the first embodiment.

In the present embodiment, the gasket 51 is attached to the slider 31 as a sealing material. The present invention, however, is not limited thereto. Any sealing material that can form a liquid-tight seal with the inner peripheral surface of the cylinder part 23 may be attached to the slider 31. For example, an annular gasket having no bottom plate similar to the gasket 50 of the first embodiment may be attached to the outer peripheral surface of the slider 31. Alternatively, any O ring similar to the O ring 52 may be attached to the outer peripheral surface of the slider 31. In these cases, an O ring that can form a liquid-tight seal with the outer peripheral surface of the first rod 41 is preferably attached to the inner peripheral surface of the through hole 31a of the slider 31 or the lower end of the inner peripheral surface of the second guide hole 72 of the top cap 260.

2.2. Usage

The usage of the device 2 is described.

The collected blood is injected to the storage vessel 20 of the empty device 2 (see FIGS. 12, 13, and 20) in the initial state. Subsequently, centrifugal separation is performed. The blood is centrifugally separated into the blood plasma component to be stored in the first storage part 21, the buffy coat (the leukocyte component and the platelet) to be stored in the cylinder part 23, and the erythrocyte component to be stored in the auxiliary storage part 24. The above described operation is substantially the same as in the first embodiment.

In the initial state, the first locking member 210 is engaged with the first rod 41 that holds the slider 31, and the first locking mechanism is in the locked state where the first locking mechanism is effectively functioned. Furthermore, the blocking member 32 is in contact with the bottom plate 24b of the auxiliary storage part 24. Thus, even when the centrifugal force F acts during the centrifugal separation (see FIG. 13), the slider 31 and the blocking member 32 do not move from the initial position.

After the centrifugal separation, a main tube 155c of the blood component recovery device (see FIG. 11) described in the description of the first embodiment is connected to the upper end of the second rod 42.

Subsequently, the upper end of the second rod 42 is gripped and the second rod 42 is pulled upward. At this time, for preventing the slider 31 from rising together with the rising second rod 42, the first rod 41 or the first locking member 210 may be pressed downward by a hand different from the hand gripping the second rod 42 as needed. When the second rod 42 is pulled up, the blocking member 32 attached to the lower end of the second rod 42 moves upward in the auxiliary storage part 24. Then, as shown in FIG. 21A, the blocking member 32 is fitted into the opening on the auxiliary storage part 24 side of the cylinder part 23 to close the opening. The O ring 52 attached to the blocking member 32 forms a liquid-tight seal with the inner peripheral surface of the cylinder part 23. As a result, the communication between the cylinder part 23 and the auxiliary storage part 24 is liquid-tightly blocked by the blocking member 32.

Figure 21B:
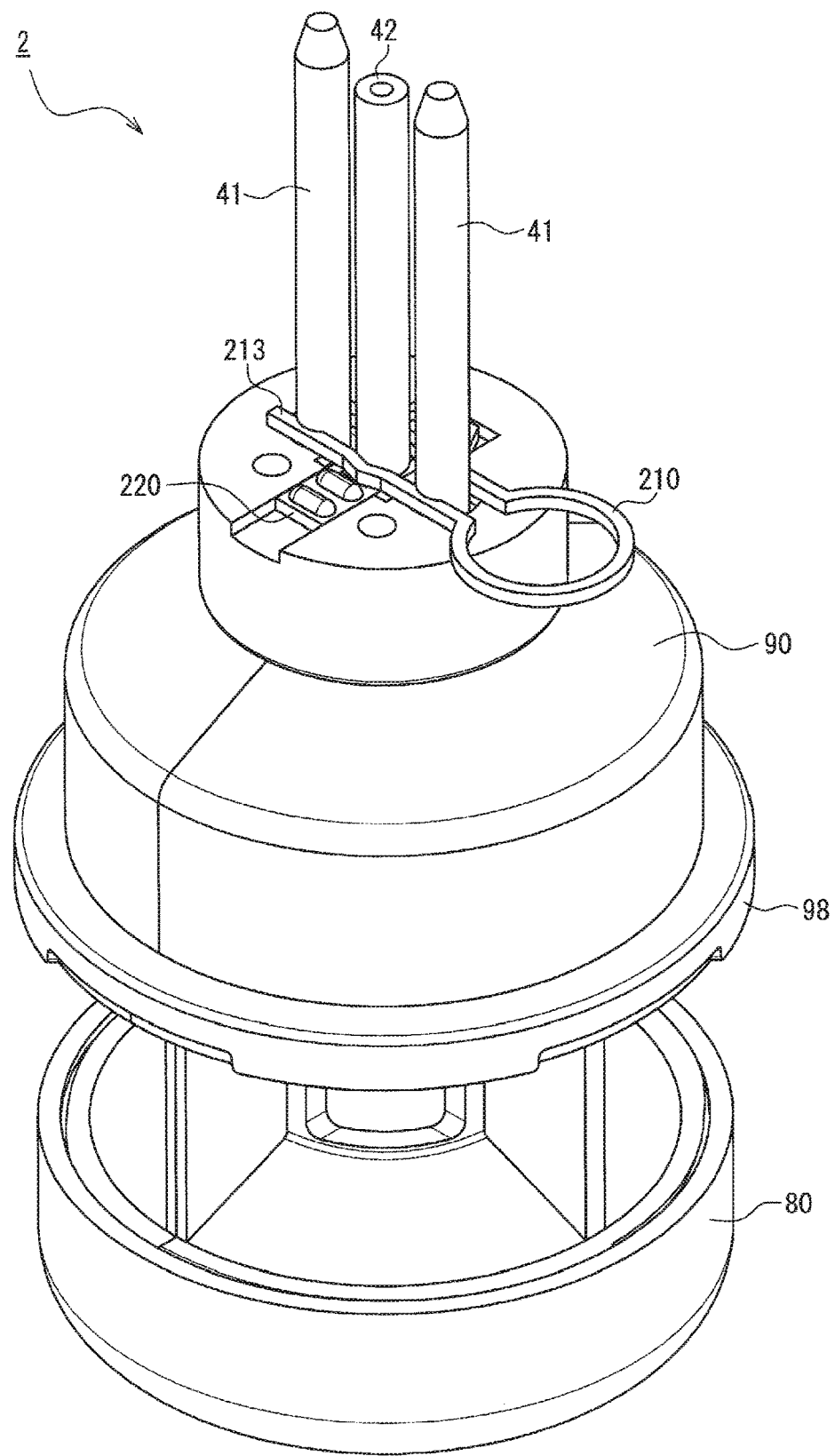
FIG. 21B is a perspective view of the device shown in FIG. 21A.

In the state where the blocking member 32 closes the lower opening of the cylinder part 23, as shown in FIG. 21B, the second locking member 220 is moved in the horizontal direction so that the second rod 42 is positioned between two locking bars 223. The second locking groove 42g of the second rod 42 (see FIG. 16A) is provided at such a position as to be at the same level as the second locking member 220 when the blocking member 32 closes the lower opening of the cylinder part 23. Therefore, as shown in FIG. 21A, the locking bar 223 of the second locking member 220 is fitted into the second locking groove 42g, and the second locking mechanism in the locked state. Even when a downward force is applied to the second rod 42, the blocking member 32 does not descend and the lower opening of the cylinder part is not opened unless the locked state of the second locking mechanism is released.

In contrast to the above, before moving the second rod 42 upward, the second locking member 220 may be moved in the horizontal direction so that the second rod 42 is positioned between two locking bars 223 in the same manner as described above. By the second rod 42, the frame 222 of the second locking member 220 (see FIG. 19) is elastically deformed so that the distance between the two locking bars 223 increases. In this state, the second rod 42 is raised while pressing the second locking member 220 through the first locking member 210 so as not to raise the second locking member 220. When the second locking groove 42g rises to the position of the locking bar 223, the frame 222 is elastically restored, the locking bar 223 is fitted into the second locking groove 42g, and the second locking mechanism is in the locked state. At the same time, the blocking member 32 liquid-tightly closes the opening on the auxiliary storage part 24 side of the cylinder part 23. According to this method, the lower opening of the cylinder part 23 is liquid-tightly closed with the blocking member 32 by fitting the locking bar 223 into the second locking groove 42g. Thus, the operation of blocking the communication between the cylinder part 23 and the auxiliary storage part 24 can be performed easily and stably regardless of the skill of the operator.

Figure 22:
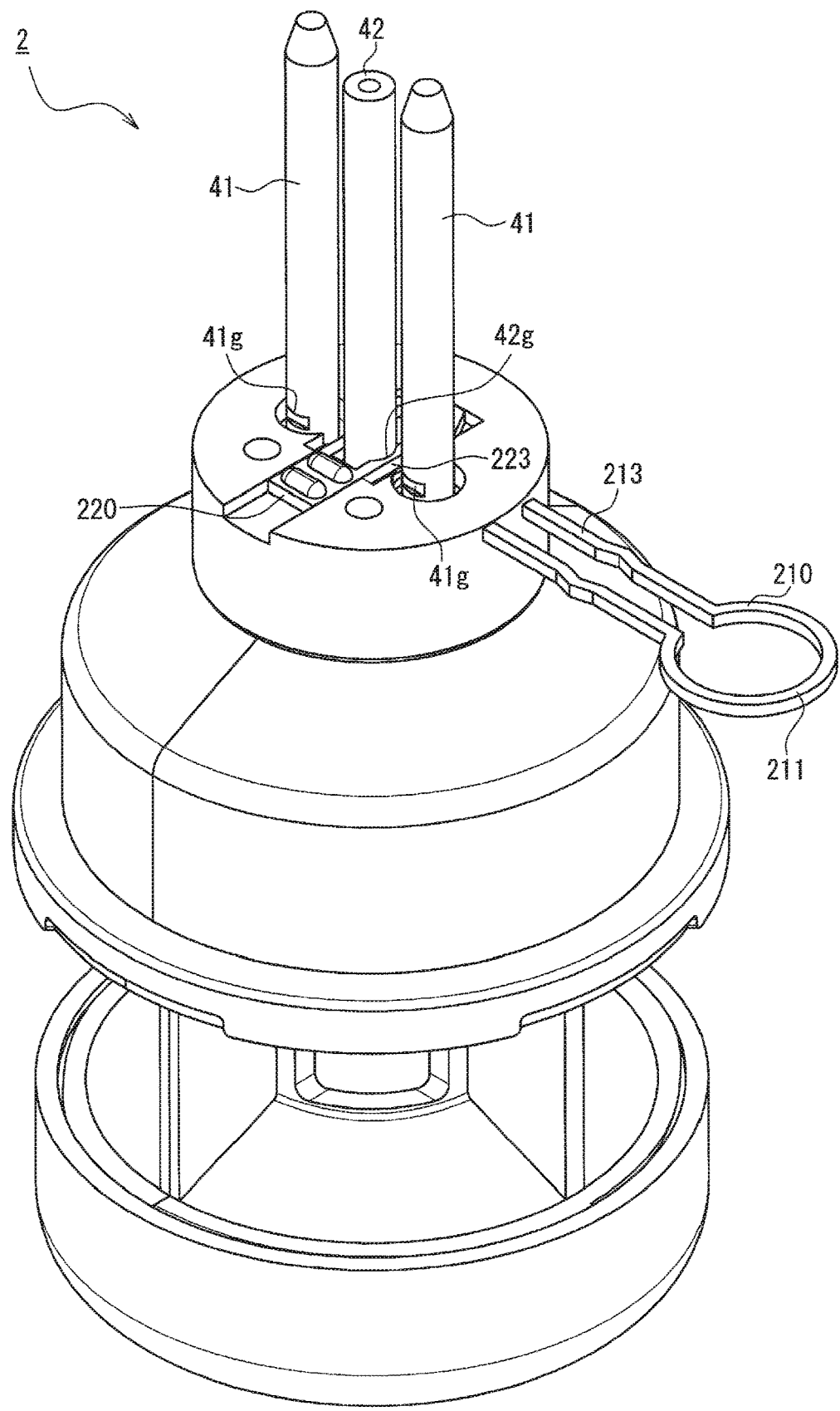
FIG. 22 is a cross sectional view of the device according to the second embodiment of the present invention in the state where a first locking member is withdrawn.

Subsequently, as shown in FIG. 22, the first locking member 210 is pulled out of the first rod 41 by gripping the operation part 211 and pulling the first locking member 210 in the horizontal direction. Thereby, the engagement between the first locking member 210 and the first locking groove 41g is released, and the first locking mechanism is in the unlocked state.

Figure 23:
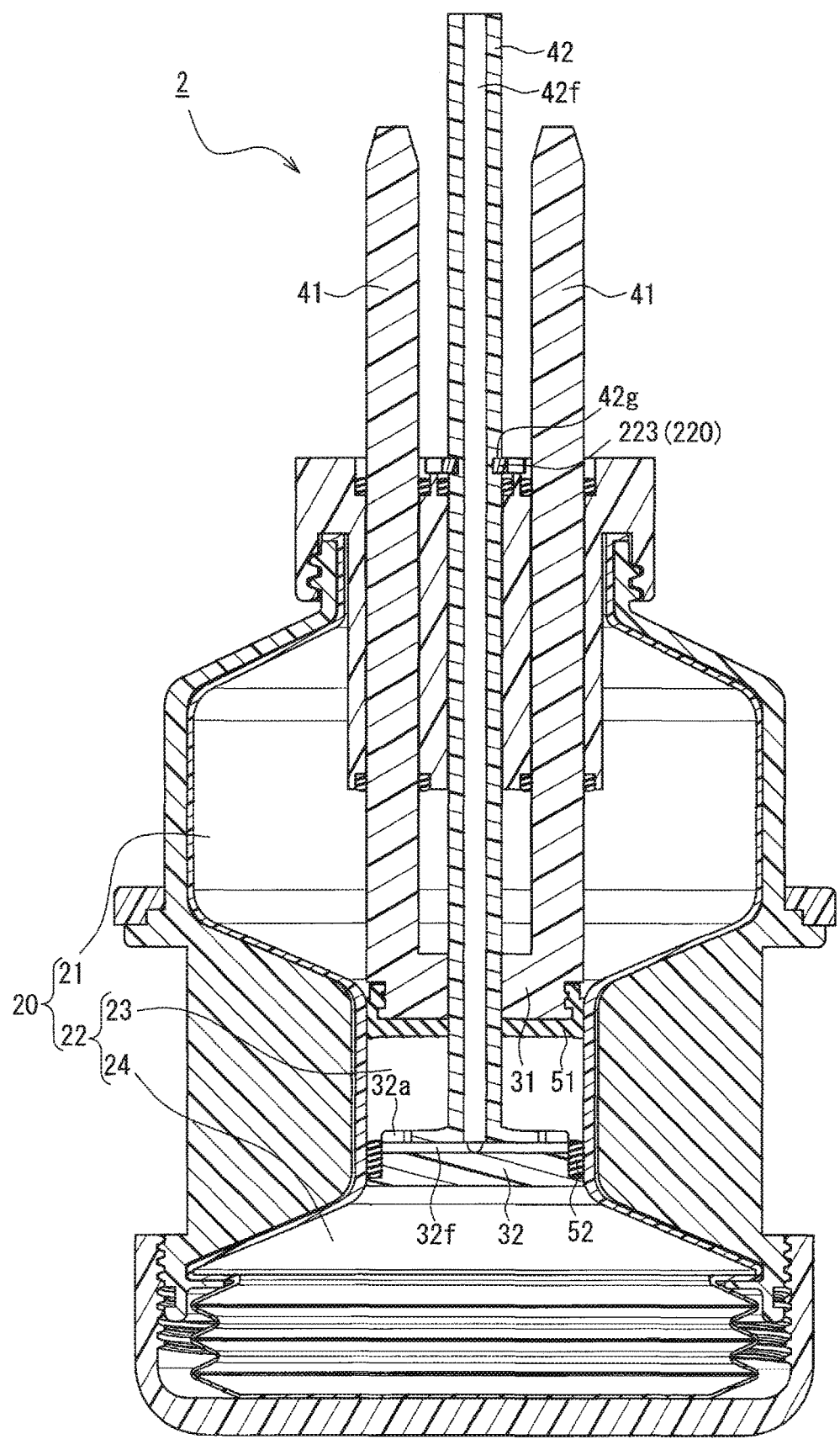
FIG. 23 is a cross sectional view of the device according to the second embodiment of the present invention in the state where communication between a first storage part and a cylinder part is blocked with a blocking member.

Subsequently, the two first rods 41 are together pushed downward. Together with the first rod 41, the slider 31 provided at the lower end of the first rod 41 also moves downward. As shown in FIG. 23, the slider 31 is fitted into the upper opening (the opening on the first storage part 21 side) of the cylinder part 23. A liquid-tight seal is formed between the gasket 51 provided on the slider 31 and the inner peripheral surface of the cylinder part 23. As a result, the communication between the first storage part 21 and the second storage part 22 (cylinder part 23) is liquid-tightly blocked by the slider 31.

The first rod 41 is further pushed downward. The slider 31 moves downward in the cylinder part 23 while maintaining the liquid-tight seal between the slider 31 and the inner peripheral surface of the cylinder part 23. As the slider 31 enters the cylinder part 23 (i.e., as the slider 31 moves away from the first storage part 21), the volume of the cylinder part 23 decreases. Thus, the blood component (e.g., the leukocyte component) in the cylinder part 23 flows into the opening 32a of the blocking member 32 and flows out of the storage vessel 20 through the flow paths 32f and 42f (see FIGS. 16A and 16B). In accordance with the descent of the slider 31, the outside air flows into the first storage part 21 through the vent port 64b (see FIG. 17A). This allows the operation of pushing down the first rod 41 and the slider 31 to be performed easily.

As described above, the second locking member 220 and the second locking groove 42g of the second rod 42 are engaged, and the second locking mechanism is still in the locked state. Therefore, even if a downward force is erroneously applied to the second rod 42 when the first rod 41 is pushed down or the pressure in the cylinder part 23 is increased in the process of descending the slider 31 in the cylinder part 23, an operation mistake such that the locking member 32 comes out of the lower opening of the cylinder part 23 does not happen.

Figure 24:
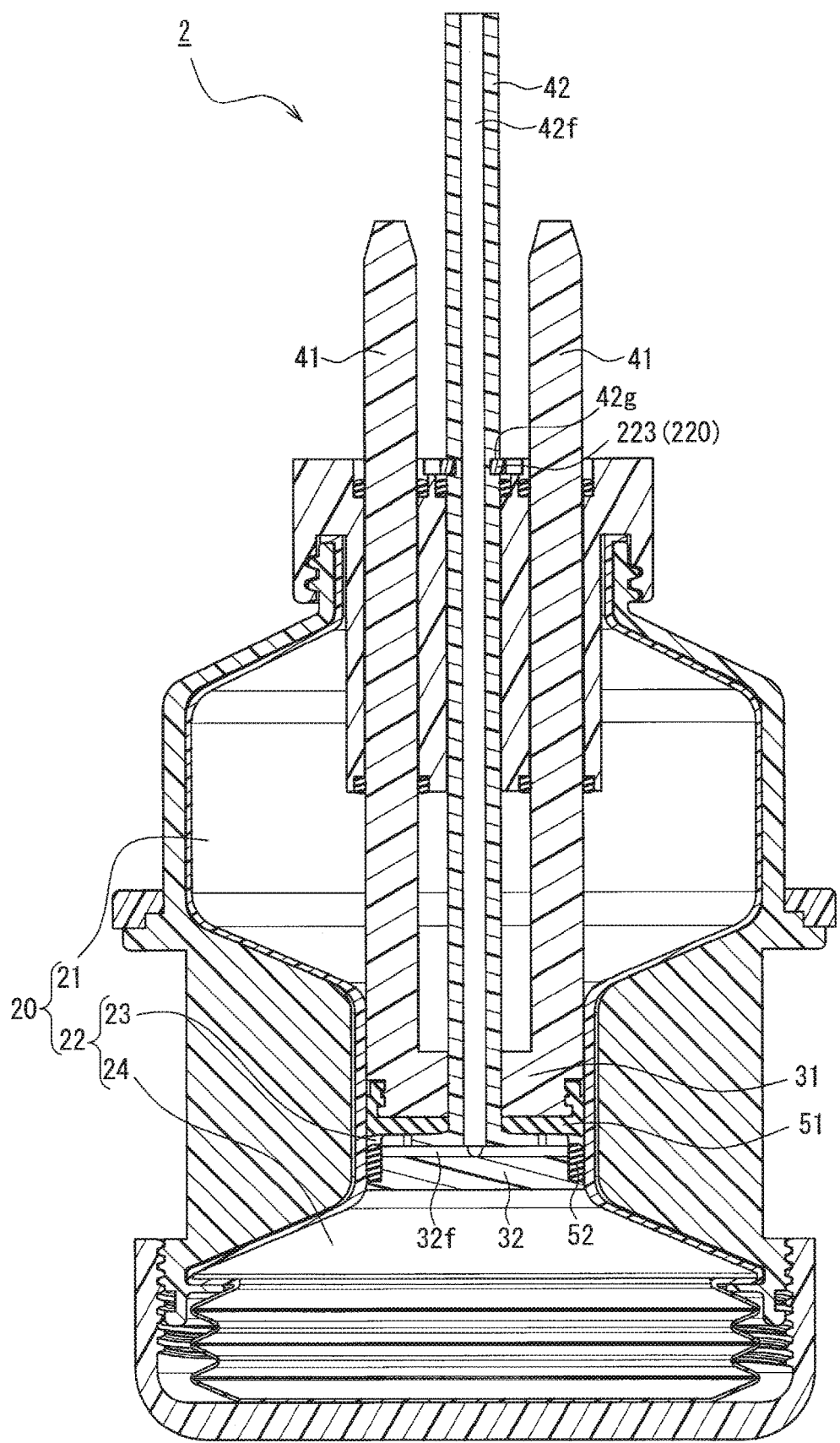
FIG. 24 is a cross sectional view of the device according to the second embodiment of the present invention after completion of recovery of a leukocyte component.

The descent of the slider 31 is stopped when all of the leukocyte component in the cylinder part 23 flows out of the storage vessel 20, thereby completing the recovery operation of the leukocyte component. FIG. 24 is a cross sectional view showing the device 2 in this state. The slider 31 (or the gasket 51) approaches or is in contact with the blocking member 32.

The blood component flowing out of the cylinder part 23 through the flow path 42f flows to the recovery device 150 (see FIG. 11). By switching the opening and closing of the clamps 157a and 157b depending on the blood component flowing through the tube 155, the leukocyte component can be recovered in the second container 152. When the lower opening of the cylinder part 23 is closed with the blocking member 32 and the slider 31 is inserted into the upper opening of the cylinder part 23 (see FIG. 23), there may be a case in which a thin erythrocyte component layer is present right above the blocking member 32, a thin blood plasma component layer is present right under the slider 31, and a leukocyte component layer is present between them. Unlike the device 1 of the first embodiment, in the device 2, the blood component in the cylinder part 23 flows to the recovery device 150 through the opening 32a of the blocking member 32. Thus, in the above-described case, the erythrocyte component, the leukocyte component, and the blood plasma component flow out of the cylinder part 23 in this order. By closing the clamp 157a and opening the clamp 157b only during flow of the leukocyte component through the tube 155, the leukocyte component can be recovered in the second container 152.

2.3. Action

As described above, the device 2 of the second embodiment includes the blocking member 32 configured to liquid-tightly block the communication between the cylinder part 23 and the auxiliary storage part 24 in addition to the slider 31 in the storage vessel 20. After the centrifugal separation, the communication between the cylinder part 23 and the auxiliary storage part 24 is blocked by the blocking member 32. Thereafter, the slider 31 is inserted into the cylinder part 23 from the first storage part 21. As the slider 30 enters the cylinder part 23, the blood component present between the slider 31 and the blocking member 32 in the cylinder part 23 can be pushed out of the storage vessel 20 through the flow paths 32f and 42f. When the blood is centrifugally separated such that the leukocyte component is present in the cylinder part 23 right before the insertion of the slider 30 into the cylinder part 23, the leukocyte component can be recovered through the flow paths 32f and 42f.

As in the first embodiment, the slider 31 slides on the inner peripheral surface in such a manner that the liquid-tight seal between the slider 31 and the inner peripheral surface of the cylinder part 23 is maintained. Thus, the leukocyte component attached to the inner peripheral surface of the cylinder part 23 is scraped (or scraped off) by sliding the slider 31. After the slider 31 has passed, almost no leukocyte component remains on the inner peripheral surface of the cylinder part 23. Therefore, the device 2 is advantageous in improving the recovery rate of the leukocyte component.

Furthermore, according to the second embodiment, the recovery rate of the leukocyte component can be improved without performing a washing step with physiological saline and a centrifugal separation of the physiological saline recovered after washing, which have been performed in the case of using the conventional device (see Patent Literature 1). Accordingly, by using the device 2, the leukocyte component can be recovered efficiently.

Because the leukocyte component in the third storage part is sucked by the syringe in the state where the upper and lower openings of the third storage part (corresponding to the cylinder part 23 of the first embodiment) of the storage vessel are closed, in addition to the flow path for allowing the leukocyte component to flow out of the third storage part, the conventional device is required to be provided with an air flow path for allowing the air to flow into the third storage part in accordance with the outflow of the leukocyte component so that a negative pressure is not caused in the third storage part. In contrast, according to the present embodiment, because the leukocyte component is extruded by the slider 30 to be recovered, the air flow path leading to the second storage part 22 (cylinder part 23) is unnecessary. As a result, the device 2 of the second embodiment has a structure simpler than the conventional device.

By connecting the recovery device 150 (see FIG. 11) to the device 2, the leukocyte component can be recovered in the same manner as in the first embodiment. When the lower opening of the cylinder part 23 is blocked with the blocking member 32 and the slider 31 is inserted into the upper opening of the cylinder part 23 (see FIG. 23), a leukocyte component of high purity in which an erythrocyte component and a blood plasma component are substantially not mixed can be recovered in the second container 152 by appropriately switching the switching mechanism (the clamps 157a and 157b) even when the erythrocyte component layer is present right above the blocking member 32 and the blood plasma component layer is present right under the slider 31. As in the first embodiment, this makes it possible to omit the step of calculating the amounts of the erythrocyte component and the blood plasma of the collected blood and to ease the adjustment accuracy of the compressive deformation amount of the bellows structure 28, which allows the recovery operation of the leukocyte component to be simplified.

Unlike the first embodiment, the device 2 of the second embodiment includes the blocking member 32 that blocks the communication between the cylinder part 23 and the auxiliary storage part 24. Thus, once the communication between the cylinder part 23 and the auxiliary storage part 24 is blocked by the blocking member 32, the leukocyte component in the cylinder part 23 and the erythrocyte component in the auxiliary storage part 24 will not be mixed thereafter due to the change of the attitude (inclination) of the device 2 and the insertion of the slider 31 into the cylinder part 23. Thus, the recovery rate of the leukocyte component can be improved stably even by an unskilled operator.

The second embodiment is the same as the first embodiment except for the above-described matters. The description of the first embodiment can be appropriately applied to the second embodiment.

3. Various Modified Embodiments

The first and second embodiments are merely examples. The present invention is not limited to the above-described first and second embodiments and can be appropriately changed.

In the first and second embodiments described above, the second storage part 22 includes the cylinder part 23 and the auxiliary storage part 24 having different inner diameters. It, however, is not necessary for the second storage part 22 to have such parts having different inner diameters.

For example, in the first embodiment including no blocking member 32, the auxiliary storage part 24 may have the same inner diameter as the cylinder part 23. In this case, there is no apparent distinction between the cylinder part 23 and the auxiliary storage part 24, and the inner diameter of second storage part 22 is constant in the central axis 1a direction (except for the bellows structure 28). Even in such a case, when the slider 30 is moved to the boundary between the leukocyte component layer and the erythrocyte component layer in the second storage part 22 after the centrifugal separation, the leukocyte component can be recovered. It is to be noted that, because the amount of the erythrocyte component contained in blood is larger than that of the leukocyte component contained in blood, as in the first embodiment, providing the auxiliary storage part 24 having a diameter larger than that of the cylinder part 23 in the second storage part 22 is advantageous for reducing the height (dimension along the central axis 1a) of the storage vessel 20 and the device 1.

In the second embodiment, the blocking member 32 movable in the second storage part 22 is used as a unit for dividing the second storage part 22 liquid-tightly at the boundary between the leukocyte component layer and the erythrocyte component layer or in the vicinity thereof after the centrifugal separation. The present invention, however, is not limited thereto.

For example, the unit for dividing the second storage part 22 may be configured with a balloon that can be inflated in the horizontal direction. The balloon is preliminarily fixed in the vicinity of the boundary between the leukocyte component layer and the erythrocyte component layer. Centrifugal separation of blood is performed in the state where the balloon is deflated, and then the balloon is inflated to form a liquid-tight seal between the balloon and the inner peripheral surface of the second storage part 22, thereby dividing the second storage part 22 into two. Air or liquid (water, physiological saline, etc.) for inflating the balloon can be supplied from the outside of the device 2 through a tube or the like. In the case of not using the blocking member 32 that rises and descends in the auxiliary storage part 24 as in this structure, also in the second embodiment, it is not necessary to make the inner diameter of the second storage part 22 different between the cylinder part 23 and the auxiliary storage part 24.

A flow path for communicating the inside and the outside of the storage vessel 20 and recovering the leukocyte component is provided in the rod 40 that holds the slider 30 in the first embodiment and is provided in the second rod 42 that holds the blocking member 32 in the second embodiment. The flow path of the present invention, however, is not limited thereto.

For example, in the first and second embodiments, the sliders 30 and 31 are provided with through holes that penetrate the sliders 30 and 31, flexible tubes are connected to the through holes, and the tubes may be led out to the storage vessel 20. Providing the flow path outside the rods 40 and 42 in this manner makes it possible to use solid members as the rods 40 and 42, which is advantageous for improving the strength of the rods 40 and 42.

In the second embodiment, as in the first embodiment, a flow path may be formed in the slider 31 and the first rod 41 that holds the slider 31.

Commonly, the structure of the first embodiment of recovering the leukocyte component from the slider 30 side positioned above the leukocyte component layer is advantageous for recovering the leukocyte component of high purity as compared to the structure of the second embodiment of recovering the leukocyte component from the blocking member 32 side positioned below the leukocyte component layer because mixing of different blood components into the leukocyte component in the flow path is reduced. That is, in the first embodiment, as the slider 30 descends in the cylinder part 23, there may be a case in which the blood plasma component flows through the flow path 40f first and subsequently the leukocyte component flows through the flow path 40f. In this case, a mixing amount of the blood plasma component into the leukocyte component in the flow path 40f is relatively small. In contrast, in the second embodiment, as the slider 31 descends in the cylinder part 23, there may be a case in which the erythrocyte component flows through the flow paths 32f and 42f first and subsequently the leukocyte component flows through the flow paths 32f and 42f. In this case, a mixing amount of the erythrocyte component into the leukocyte component in the flow paths 32f and 42f is relatively large. Although it is not certain, this difference is thought to be due to the difference in physical properties of blood components such as specific gravity and viscosity. Therefore, in the second embodiment, the structure in which flow paths are provided through the slider 31 as in the first embodiment can be advantageous for recovering the leukocyte component of high purity. Furthermore, the structure in which the flow paths are provided in the first rod 41 that holds the slider 31 allows the flow path to be shortened as compared to the second embodiment in which the flow path is provided in the second rod 42 that holds the blocking member 32. This is advantageous in improving the recovery rate of the leukocyte component because the leukocyte component attached to the inner wall surface of the flow path can be reduced.

The structures of the locking mechanisms for the sliders 30 and 31 and the blocking member 32 are not limited to the first and second embodiments. For example, in the state where the slider 30(31) is in the initial position (see FIGS. 1, 2, 12, and 13), a projection projecting along the radial direction may be provided at the part of the rod 40(41) that projects upward from the top cap 60(260), and a detachable spacer member may be attached between the projection and the top plate 61 of the top cap 60(260). When the slider 30(31) is descended, the spacer is removed. Because this structure does not require the locking groove 40g(41g) provided on the rod 40(41), the problems such as the decrease in the strength of the rod 40(41) due to the locking groove 40g(41g) and the decrease in the operability of the operation of descending the slider 30(31) due to interference between the locking groove 40g(41g) and the O ring(s) 54(55a, 55b, 57a, and 57b) can be solved. Similarly, in the state where the lower opening of the cylinder part 23 is blocked (FIGS. 21A, and 21B), a projection projecting along the radial direction may be provided at the part of the second rod 42 that projects upward from the top cap 260, and a detachable spacer may be attached between the projection and the top plate 61 of the top cap 260. Because this structure does not require the second locking groove 42g provided on the second rod 42, the problems such as the decrease in the strength of the rod 42 due to the second locking groove 42g and the decrease in the operability of the operation of raising the blocking member 32 due to interference between the second locking groove 42g and the O ring 56 can be solved.

The number of rods that hold the sliders 30 and 31 and the blocking member 32 is not limited to the above-described embodiments, and can be changed appropriately. For example, in the second embodiment, the slider 31 may be held by one first rod 41 and the blocking member 32 may be held by two second rods 42.

In the first and second embodiments, the gasket 50(51) is attached to the slider 30(31) and the O ring 52 is attached to the blocking member 32 for forming a liquid-tight seal between the gasket 50(51) and the inner peripheral surface of the cylinder part 23. It is to be noted that the gasket 50(51) and the O ring 52 can be omitted by forming the slider 30(31) and the blocking member 32 themselves with a material having rubber elasticity (also referred to as elastomer). In this case, the material having rubber elasticity that can be used is not particularly limited, and rubber such as natural rubber, isoprene rubber, or silicone rubber; or a thermoplastic elastomer such as styrene elastomer, olefin elastomer, or polyurethane elastomer can be used.

In the first and second embodiments, blood is injected into the storage vessel 20 through the injection port 64a provided on the top cap 60(260). The method of injecting blood, however, is not limited thereto. For example, blood may be injected through the flow path(s) 40f (42f and 32f) for recovering the leukocyte component or may be injected through the opening 25 of the storage vessel 20 before attaching the top cap 60(260) to the storage vessel 20. In these cases, the injection port 64a can be omitted.

The container for recovering the leukocyte component can be any container other than the recovery device 150 shown in FIG. 11.

While the bellows adjusting mechanism is configured to compress the bellows structure 28 in the vertical direction and adjust the amount of compression thereof in the first and second embodiments, the bellows adjusting mechanism may be configured to expand the bellows structure 28 in the vertical direction and adjust the amount of expansion thereof.

While the male screw 93 and the female screw 83 that configure the bellows adjusting mechanism for adjusting the expansion and compression amount of the bellows structure 28 are formed on the support member 90 and the bottom cap 80, respectively, in the first and second embodiments, the female screw may be formed on the support member 90 and the male screw may be formed on the bottom cap 80.

The male screw 93 may be provided on a member other than the support member 90 or the female screw 83 may be provided on a member other than the bottom cap 80. For example, at least one of the male screw 93 and the female screw 83 that configure the bellows adjusting mechanism may be provided on the storage vessel 20. For example, the male screw 93 may be provided at a higher level with respect to the bellows structure 28 of the storage vessel 20. In this case, when the storage vessel 20 has such a strength as not to be deformed by a centrifugal force during centrifugal separation, the support member 90 can be omitted. Alternatively, the male screw 93 may be provided at a lower level with respect to the bellows structure 28 of the storage vessel 20. The skirt part 92 of the support member 90 may be extended downward and a female screw may be formed on the inner peripheral surface of the skirt part 92. The expansion amount of the bellows structure 28 can be adjusted by rotating the support member 90 with respect to the storage vessel 20. In this case, the bottom cap 80 can be omitted.

While the bellows adjusting mechanism is configured to adjust the compression amount of the bellows structure 28 by the rotational position between the support member 90 and the bottom cap 80 and the engagement depth between the male screw 93 and the female screw 83 in the first and second embodiments, the compression amount of the bellows structure 28 may be adjusted by a method other than this. For example, there may be a method of engaging the support member 90 and the bottom cap 80 by interposing the plate-like member having a thickness corresponding to the required compression amount of the bellows structure 28 between the bottom plate 80b of the bottom cap 80 and the bottom plate 24b of the storage vessel 20. The compression amount of the bellows structure 28 can be adjusted by changing the number of plate-like members to be stacked or replacing with the plate-like members having different thicknesses. Because the bottom plate 80b of the bottom cap 80 is substantially raised by the plate-like member according to this method, without adjusting the engagement depth, the bellows structure 28 can be compressed by a desired amount at the time when the bottom cap 80 is attached to the support member 90.

The volume adjusting mechanism for adjusting the volume of the storage vessel 20 is not limited to the bellows structure 28. For example, the volume adjusting mechanism can be configured with a diaphragm, a piston, a balloon, or the like. The volume adjusting mechanism can be provided, for example, in or adjacent to the auxiliary storage part 24. The volume of the storage vessel 20 can be adjusted using the volume adjusting mechanism such that the buffy coat is formed in the cylinder part 23 after centrifugal separation by obtaining the hematocrit value of the blood before centrifugal separation.

In the above-described usage of the first embodiment, for pushing the leukocyte component out of the storage vessel 20, the slider 30 is descended by the cylinder part 23. However, the method of recovering the leukocyte component outside the storage vessel 20 using the device 1 of the first embodiment is not limited to this. That is, as shown in FIG. 9, in the state where the slider 30 is fitted into the upper opening (the opening on the first storage part 21 side) of the cylinder part 23 to block the communication between the first storage part 21 and the second storage part 22, the volume of the second storage part 22 may be reduced by using the volume adjusting mechanism (the bellows structure 28). As the volume of the second storage part 22 decreases, the blood component (e.g., leukocyte component) in contact with the lower surface of the slider 30 can flow out of the storage vessel 20 through the flow path 40f. In this usage of the device 1 (hereinafter, referred to as "another usage"), it is not required to move the slider 30 in the cylinder part 23 while maintaining a liquid-tight seal between the slider 30 and the inner peripheral surface of the cylinder part 23. Because this makes it possible to ease the accuracy of the inner peripheral surface of the cylinder part 23, this is advantageous for efficiently and inexpensively producing the entire storage vessel 20, for example, by a blow molding method or the like. It is to be noted that, in another usage, because the slider 30 does not move in the cylinder part 23, unlike the usage of the first embodiment, the slider 30 does not scrapes off the leukocyte component attached to the inner peripheral surface of the cylinder part 23. However, because the volume of the auxiliary storage part 24 is reduced using the volume adjusting mechanism in the state where the lower opening (opening on the auxiliary storage part 24 side) of the cylinder part 23, the possibility of unintentionally mixing the leukocyte component with the erythrocyte component is low. From this point of view, another usage of the device 1 can improve the recovery rate of the leukocyte component as compared to the case of using a conventional device.

In the present invention, the volume adjustment mechanism for adjusting the volume of the storage vessel 20 may be omitted. However, when the above-described another method is performed using the device 1, the volume adjustment mechanism cannot be omitted.

The structure of the support member 90 for maintaining the shape of the storage vessel 20 is not limited to the above-described examples, and can be any structure. For example, the support member is not limited to the one divided into two in the circumferential direction as in the first and second embodiments, and the support member may be divided into three or more in the circumferential direction. The support member may be configured with a plurality of columnar members spaced from each other in the circumferential direction. In the case where the storage vessel 20 has such a strength as not to be deformed by a centrifugal force during the centrifugal separation, for example, by integrally forming a support member on the parts that configure the storage vessel 20, a support member as a separate member from the storage vessel 20 may be omitted.

INDUSTRIAL APPLICABILITY

The application field of the present invention is not particularly limited, and can be widely used in the medical field where blood is required to be centrifugally separated. In particular, the present invention can be preferably used in the fields of separation of blood components in the case of performing component transfusion of transfusing only necessary components in blood to a patient, bone marrow transplantation mainly using the leukocyte component, and regenerative medicine.

REFERENCE SIGNS LIST 1, 2 blood component separator
20 blood storage vessel
21 first storage part
22 second storage part
23 cylinder part
24 auxiliary storage part
28 bellows structure (volume adjusting mechanism)
30, 31 slider
32 blocking member
40f, 32f, 42f flow path
40 rod (first rod)
40g locking groove (first locking mechanism)
41 first rod
41g first locking groove (first locking mechanism)
42 second rod
42g second locking groove (second locking mechanism)
110 locking member (first locking mechanism)
150 blood component recovery device
151 first container
152 second container
157a, 157b clamp (switching mechanism)
210 first locking member (first locking mechanism)
220 second locking member (second locking mechanism)

The invention claimed is:

1. A blood component separator for use in centrifugal separation of blood, comprising:
   a blood storage vessel including a first storage part and a second storage part;
   a slider movable from the first storage part to the second storage part; and
   a flow channel provided at least through the slider for communicating an inside and an outside of the storage vessel, wherein
   when the slider is in the first storage part, the first storage part and the second storage part are in communication with each other,
   when the slider is inserted into the second storage part, a liquid-tight seal is formed between the slider and an inner peripheral surface of the second storage part and the communication between the first storage part and the second storage part is blocked by the slider,
   the slider is movable in the second storage part while maintaining the liquid-tight seal between the slider and the inner peripheral surface of the second storage part, and
   as the slider enters into the second storage part, a blood component in the second storage part is pushed out of the storage vessel through the flow channel.

2. The blood component separator according to claim 1, further comprising:
   a first rod holding the slider and that extends out of the storage vessel, wherein
   the flow channel is provided through the first rod.

3. The blood component separator according to claim 1, further comprising:
   a first locking mechanism that restricts movement of the slider in the first storage part toward the second storage part.

4. The blood component separator according to claim 1, wherein
   the second storage part includes a cylinder part disposed adjacent to the first storage part, and
   the liquid-tight seal is formed between an inner peripheral surface of the cylinder part and the slider.

5. The blood component separator according to claim 4, wherein
   the inner peripheral surface of the cylinder part is a cylindrical surface.

6. The blood component separator according to claim 4, wherein
   the second storage part includes an auxiliary storage part communicating with the first storage part through the cylinder part, and
   the auxiliary storage part has an inner diameter larger than that of the cylinder part.

7. The blood component separator according to claim 4, wherein
   the second storage part includes an auxiliary storage part communicating with the first storage part through the cylinder part, and
   a blocking member that can block communication between the cylinder part and the auxiliary storage part is provided in the second storage part.

8. The blood component separator according to claim 7, wherein
   the blocking member is movable in the auxiliary storage part,
   when the blocking member is in the auxiliary storage part, the cylinder part and the auxiliary storage part are in communication with each other, and
   when the blocking member is fitted into an opening on an auxiliary storage part side of the cylinder part, the communication between the cylinder part and the auxiliary storage part is blocked by the blocking member.

9. The blood component separator according to claim 7, further comprising:
   a second rod holding the blocking member and that extends out of the storage vessel, wherein
   the flow channel is provided through the second rod.

10. The blood component separator according to claim 7, further comprising:
    a second locking mechanism for maintaining a state where the blocking member blocks the communication between the cylinder part and the auxiliary storage part.

11. The blood component separator according to claim 1, further comprising:
    a vent port for communicating the first storage part and the outside of the storage vessel.

12. The blood component separator according to claim 1, wherein the second storage part is provided with a volume adjusting mechanism that can adjust a volume of the storage vessel.

13. The blood component separator according to claim 1, further comprising:

a blood component recovery device configured to recover the blood component pushed out of the storage vessel through the flow channel, wherein the recovery device includes a first container, a second container, and a switching mechanism configured to selectively communicate the flow channel with either the first container or the second container.

14. A method of separating a blood component using the blood component separator according to claim 1, comprising:

introducing a blood into the blood storage vessel, centrifuging the blood component separator, moving the slider from the first storage part to the second storage part to form the liquid-tight seal between the slider and an inner peripheral surface of the second storage part and block the communication between the first storage part and the second storage part, and collecting the blood component through the flow channel by inserting the slider into the second storage part.

15. The method of separating a blood component according to claim 14, wherein the blood is a bone marrow aspirate.

16. The method of separating a blood component according to claim 14, wherein the slider is held by a first rod, the flow channel is formed in the slider and the first rod, and an opening of the flow channel is formed on a lower surface of the slider, wherein the method further comprises recovering a separated component from the opening on the lower surface of the slider via the flow channel by pushing the slider into the second storage part.

\* \* \* \* \*